US011937908B2

(12) United States Patent
Chauffert et al.

(10) Patent No.: US 11,937,908 B2
(45) Date of Patent: Mar. 26, 2024

(54) METHOD AND APPARATUS FOR ACCELERATED MAGNETIC RESONANCE IMAGING

(71) Applicants: COMMISSARIAT A L'ENERGIE ATOMIQUE ET AUX ENERGIES ALTERNATIVES, Paris (FR); UNIVERSITÉ PARIS-SACLAY, Saint-Aubin (FR); CENTRE NATIONAL DE LA RECHERCHE SCIENTIFIQUE, Paris (FR)

(72) Inventors: Nicolas Chauffert, Palaiseau (FR); Philippe Ciuciu, Longpont sur Orge (FR); Jonas Kahn, Toulouse (FR); Carole Lazarus, Gentilly (FR); Alexandre Vignaud, Paris (FR); Pierre Weiss, Pechbusque (FR)

(73) Assignees: COMMISSARIAT A L'ENERGIE ATOMIQUE ET AUX ENERGIES ALTERNATIVES PARIS, FRANCE, Paris (FR); UNIVERSITÉ PARIS-SACLAY, Saint-Aubin (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 1031 days.

(21) Appl. No.: 16/639,725

(22) PCT Filed: Sep. 6, 2018

(86) PCT No.: PCT/EP2018/074047
§ 371 (c)(1),
(2) Date: Feb. 17, 2020

(87) PCT Pub. No.: WO2019/048565
PCT Pub. Date: Mar. 14, 2019

(65) Prior Publication Data
US 2020/0205692 A1   Jul. 2, 2020

(30) Foreign Application Priority Data

Sep. 6, 2017  (EP) .................................... 17306151

(51) Int. Cl.
*A61B 5/055* (2006.01)
*G01R 33/48* (2006.01)
*G01R 33/561* (2006.01)

(52) U.S. Cl.
CPC .......... *A61B 5/055* (2013.01); *G01R 33/4824* (2013.01); *G01R 33/561* (2013.01)

(58) Field of Classification Search
CPC ................ A61B 5/055; G01R 33/4824; G01R 33/5611; G01R 33/56572; G01R 33/5608; G01R 33/56341
See application file for complete search history.

(56) References Cited

U.S. PATENT DOCUMENTS 9,858,689 B1 * 1/2018 Mailhe ............... G01R 33/5608
2012/0010497 A1 * 1/2012 Ehman ................. A61B 5/0051
600/410
(Continued)

FOREIGN PATENT DOCUMENTS

WO    2016/202707 A1    12/2016

OTHER PUBLICATIONS

Lazarus, et al., "SPARKLING: Novel Non-Cartesian Sampling Schemes for Accelerated 2D Anatomical Imaging at 7T Using Compressed Sensing", Proceedings of the International Society for Magentic Resonance in Medicine, vol. 25, p. 1529, Apr. 7, 2017.
(Continued)

*Primary Examiner* — Baisakhi Roy
(74) *Attorney, Agent, or Firm* — BakerHostetler

(57) ABSTRACT

A method of performing magnetic resonance imaging of a body includes a) immerging the body in a static and substantially uniform magnetic field; b) exciting nuclear spins
(Continued)

Figure 1:
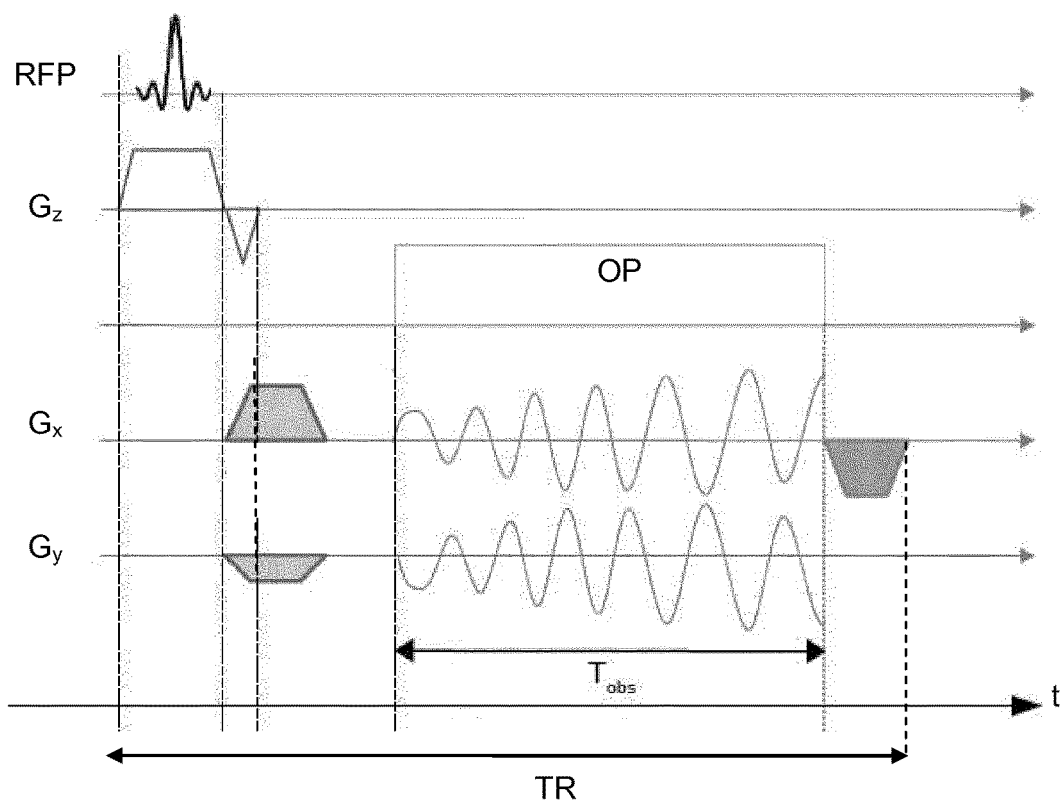

inside the body using at least one radio-frequency pulse; c) applying to the body a time-varying magnetic field gradient defining at least one trajectory (ST) in k-space and simultaneously acquiring samples of a magnetic resonance signal so as to perform a pseudo-random sampling (KS) of the k-space; and d) applying a sparsity-promoting nonlinear reconstruction algorithm for reconstructing a magnetic resonance image of the body; wherein, at least in a low-spatial frequency region of the k-space, the distance between any two adjacent points belonging to a same trajectory is lower than 1/FOV, FOV being the size of a field of view of the reconstructed image. A magnetic resonance imaging apparatus for carrying out such a method is also provided.

6 Claims, 11 Drawing Sheets

(56) References Cited

U.S. PATENT DOCUMENTS

| | | | | |
|---|---|---|---|---|
| 2013/0088225 | A1* | 4/2013 | Weller | G01R 33/5611 324/322 |
| 2013/0278257 | A1* | 10/2013 | Boada | G01R 33/56341 324/309 |
| 2013/0328919 | A1* | 12/2013 | Holt | G01N 23/04 345/629 |
| 2014/0125335 | A1 | 5/2014 | Li et al. | |
| 2014/0212012 | A1 | 7/2014 | Fain et al. | |
| 2014/0286560 | A1* | 9/2014 | Trzasko | G01R 33/5611 382/131 |
| 2015/0032406 | A1* | 1/2015 | Grodzki | G01R 33/56572 702/123 |
| 2015/0302842 | A1* | 10/2015 | Griswold | G10H 3/12 84/604 |

OTHER PUBLICATIONS

Boyer, et al., "On the generation of sampling schemes for magnetic resonance imaging", SIAM Journal on Imaging Sciences, vol. 9, No. 4, pp. 2039-2072, Dec. 6, 2016.
Boesen, et al., "Pulsatile motion suppression using cine fast spin echo and nonlinear image reconstructions", Proceedings of the International Society for Magentic Resonance in Medicine, vol. 22, p. 4348, Apr. 25, 2014.
Zhu, et al., "GOCART: GOlden-angle CArtesian randomized time-resolved 3D MRI", Magnetic Resonance Imaging, vol. 34(7), pp. 940-950, Dec. 19, 2015.
Speidel, et al., "Accelerated Adaptive Quasi-Random Single-Point Imaging for in vivo Artefact Reduction", Proceedings of the International Society for Magentic Resonance in Medicine, vol. 25, p. 4026, Apr. 7, 2017.
Liu, et al., "Accelerated MRI with CIRcular Cartesian UnderSampling (CIRCUS): a variable density Cartesian sampling strategy for compressed sensing and parallel imaging", Quantitative Imaging in Medicine and Surgery, vol. 4, No. 1, pp. 57-67, Feb. 12, 2014.
Vasanawala, et al., "Practical parallel imaging compressed sensing MRI:Summary of two years of experience in accelerating body MRI of pediatric patients", Proceedings IEEE of the International Symp Biomedical Imaging, pp. 1039-1043, Mar. 30, 2011.
Seeger, et al., "Optimization of k-space trajectories for compressed sensing by Bayesian experimental design", Magentic Resonance in Medicine, vol. 63, pp. 116-126, Oct. 26, 2009.
Lustig, et al., "Sparse MRI: The application of compressed sensing for rapid MR imaging", Magentic Resonance in Medicine, vol. 58, No. 6, pp. 1182-1195, Oct. 29, 2007.

Vannesjo, et al., "Gradient system characterization by impulse response measurements with a dynamic field camera", Magnetic resonance in medicine, vol. 69, No. 2, pp. 583-593, Apr. 12, 2012.
Vannesjo, et al.,"Image reconstruction using a gradient impulse response model for trajectory prediction", Magnetic resonance in medicine, vol. 76, No. 1, pp. 45-58, Jul. 27, 2015.
Arias-Castro, et al., "On the fundamental limits of adaptive sensing", IEEE IEEE Transactions on Information Theory, 59, pp. 472-481, 2013.
Beck, et al., "A fast iterative shrinkage-thresholding algorithm for linear inverse problems", SIAM journal on imaging sciences 2.1, pp. 183-202, 2009.
Bilgin, et al., "Randomly perturbed radial trajectories for compressed sensing MRI." Proceedings of ISMRM, Toronto, Canada, p. 3152, 2008.
Chauffert, et al., "Variable density sampling with continuous trajectories", SIAM Journal on Imaging Sciences 7.4, pp. 1962-1992, 2014.
Curtis, et al., "Random volumetric MRI trajectories via genetic algorithms", International Journal of Biomedical Imaging, 2008.
Dippe, et al., "Antialiasing through stochastic sampling." ACM Siggraph Computer Graphics 19.3, pp. 69-78, 1985.
Feng, et al., "Xd-grasp: Golden-angle radial MRI with reconstruction of extra motion-state dimensions using compressed sensing," Magnetic resonance in medicine, vol. 75, No. 2, pp. 775-788, 2016.
Haldar, et al., "Compressed-Sensing MRI with Random Encoding", IEEE Transaction of Medical Imaging 30, pp. 893-903, 2011.
Haldar, et al., "Low-Rank Modeling of Local k-Space Neighborhoods (LORAKS) for Constrained MRI", IEEE Transaction of Medical Imaging, vol. 33, No. 3, pp. 668-680, 2014.
Liu, et al., "Under-sampling trajectory design for compressed sensing MRI", in 2012 Annual International Conference of the IEEE Engineering in Medicine and Biology Society (EMBC), pp. 73-76, 2012.
Lloyd, "Least squares quantization in PCM", IEEE transactions on information theory, 28.2, pp. 129-137, 1982.
Lustig, et al., "Compressed sensing MRI", IEEE signal processing magazine 25.2, pp. 72-82, 2008.
Mir, et al., "Fast three-dimensional k-space trajectory design using missile guidance ideas", Magnetic resonance in medicine, 52, pp. 329-336, 2004.
Nayak, et al., "Randomized trajectories for reduced aliasing artifact", Proceedings of the ISMRM, Sydney, p. 670, 1998.
Pipe, et al., "Aplication to head motion and free-breathing cardiac imaging", Magnetic resonance in medicine, 42:963-9., 1999.
Ravishankar, et al., "Adaptive sampling design for compressed sensing MRI", Annual International Conference of the IEEE Engineering in Medicine and Biology Society, pp. 3751-3755, 2011.
Spiniak, et al., "Undersampling k-space using fast progressive 3D trajectories", Magnetic resonance in medicine, 54, pp. 886-892, 2005.
Wang, et al., "Image Quality Assessment: From Error Visibility to Structural Similarity", IEEE Transactions on Image Processing, vol. 13, No. 4, Apr. 2004.
Wang, et al., "Smoothed random-like trajectory for compressed sensing MRI", Engineering in Medicine and Biology Society (EMBC), 2012 Annual International Conference of the IEEE, IEEE, pp. 404-407, 2012.
Notice of Rejection issued in Japanese Patent Application No. 2020-513810 dated Aug. 30, 2022, with English translation.
Lazarus, et al., "SPARKLING: Novel Non-Cartesian Sampling Schemes for Accelerated 2D Anatomical Imaging at 7T Using Compressed Sensing", 25th annual meeting of the International Society for Magnetic Resonance Imaging, USA, ISMRM, Apr. 2017.
Boyer, et al., "On the generation of sampling schemes for Magnetic Resonance Imaging", SIAM journal on Imaging Sciences, vol. 9, No. 4 , Sep. 28, 2016.

* cited by examiner

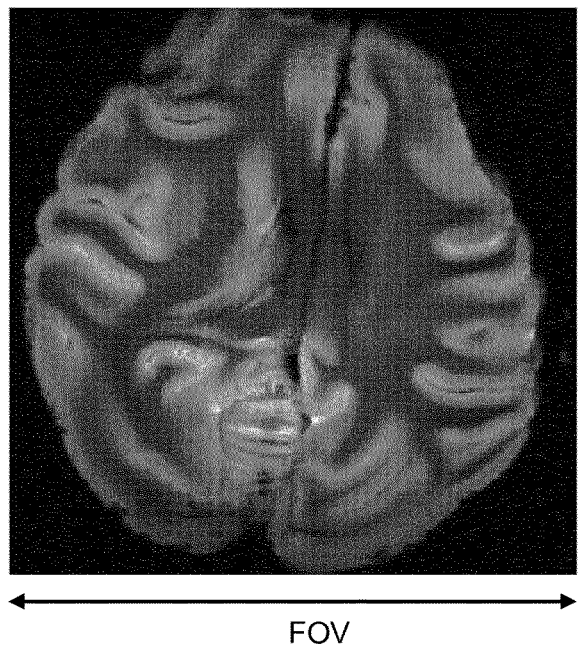
FOV
Fig. 3
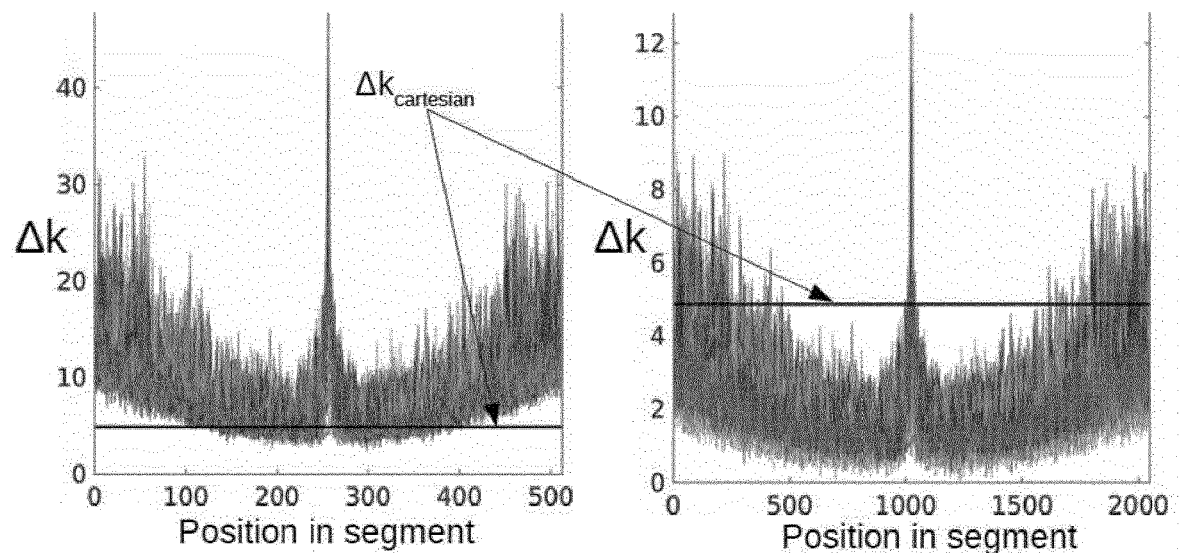
Fig. 4A
Fig. 4B

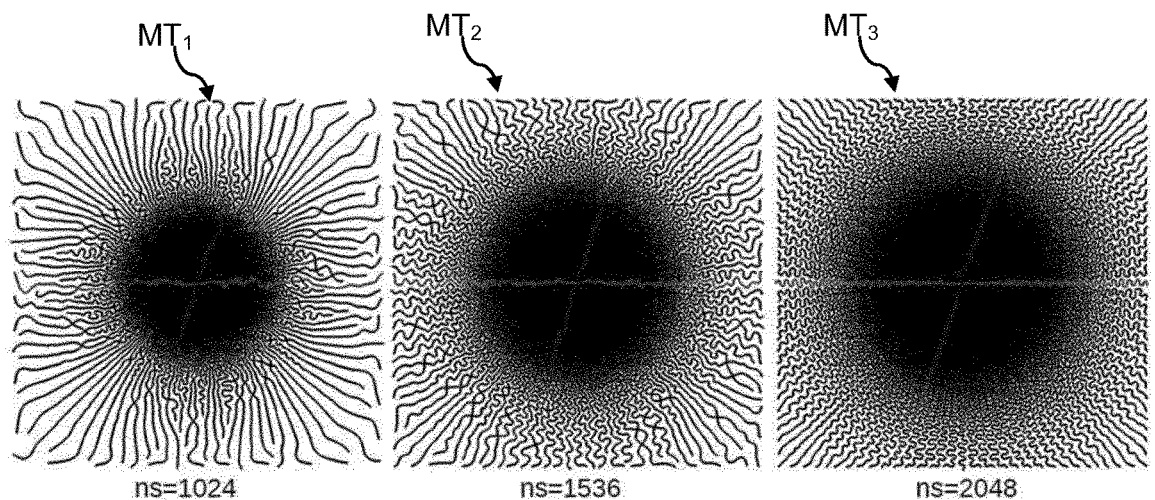
Fig. 5A  Fig. 5B  Fig. 5C
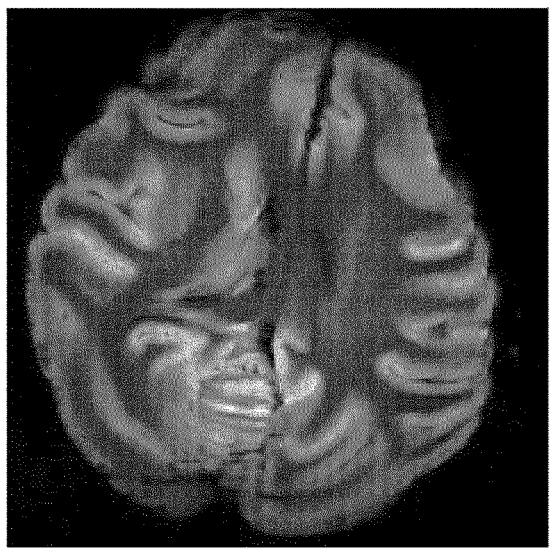 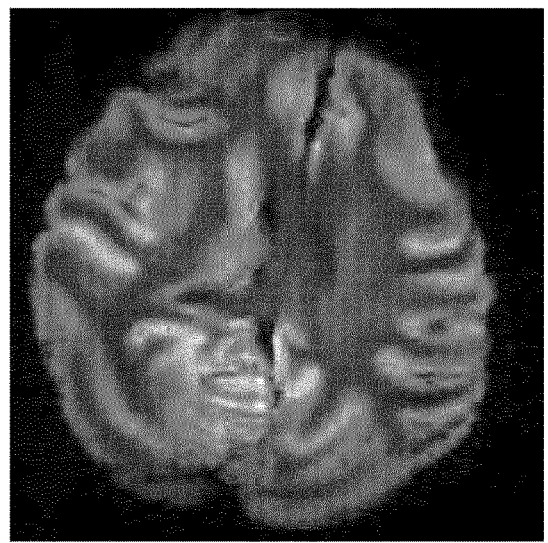
Fig. 6A  Fig. 6B

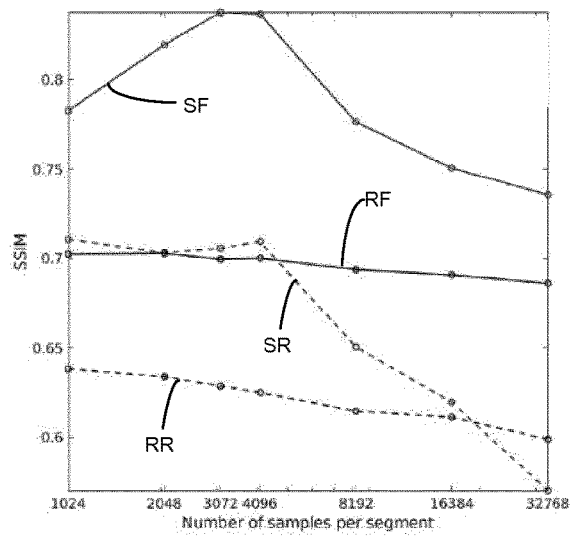
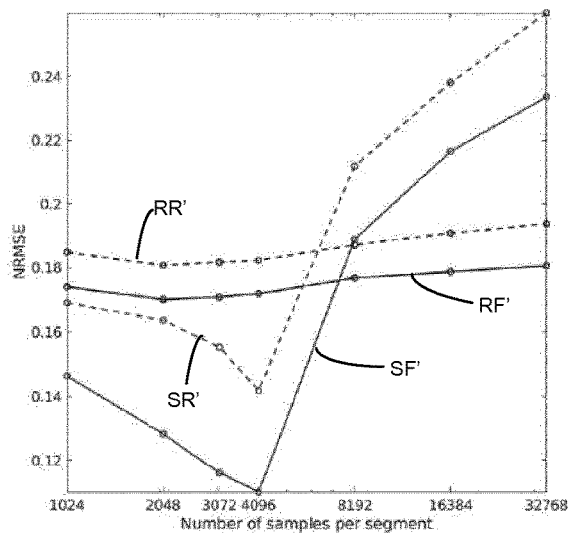
Fig. 7A
Fig. 7B
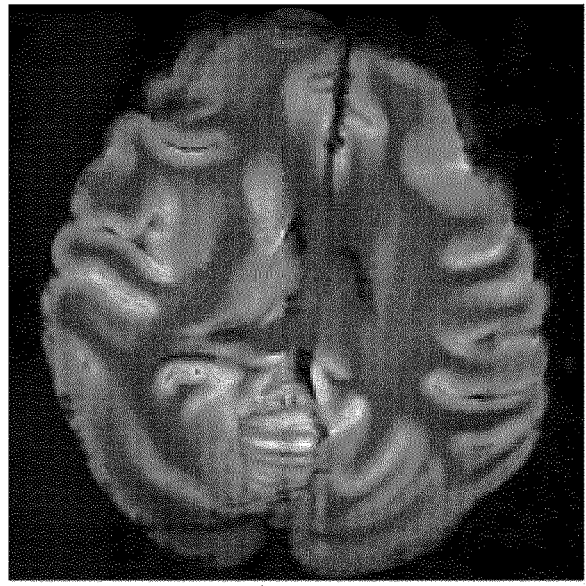
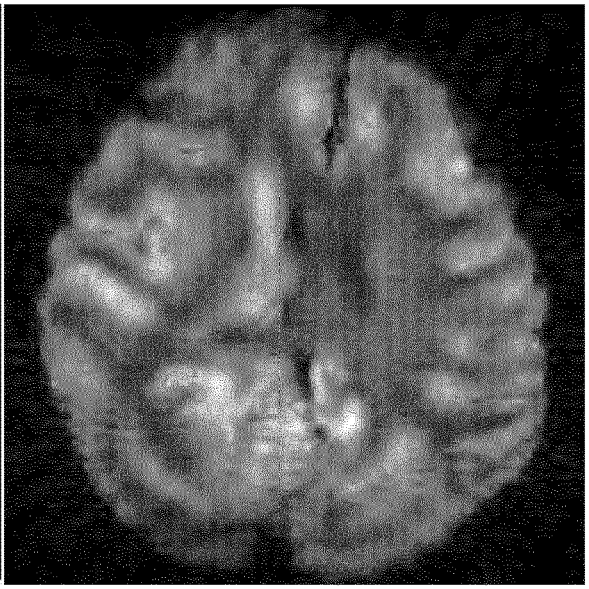
Fig. 8A
Fig. 8B

Fig. 9A                                    Fig. 9B

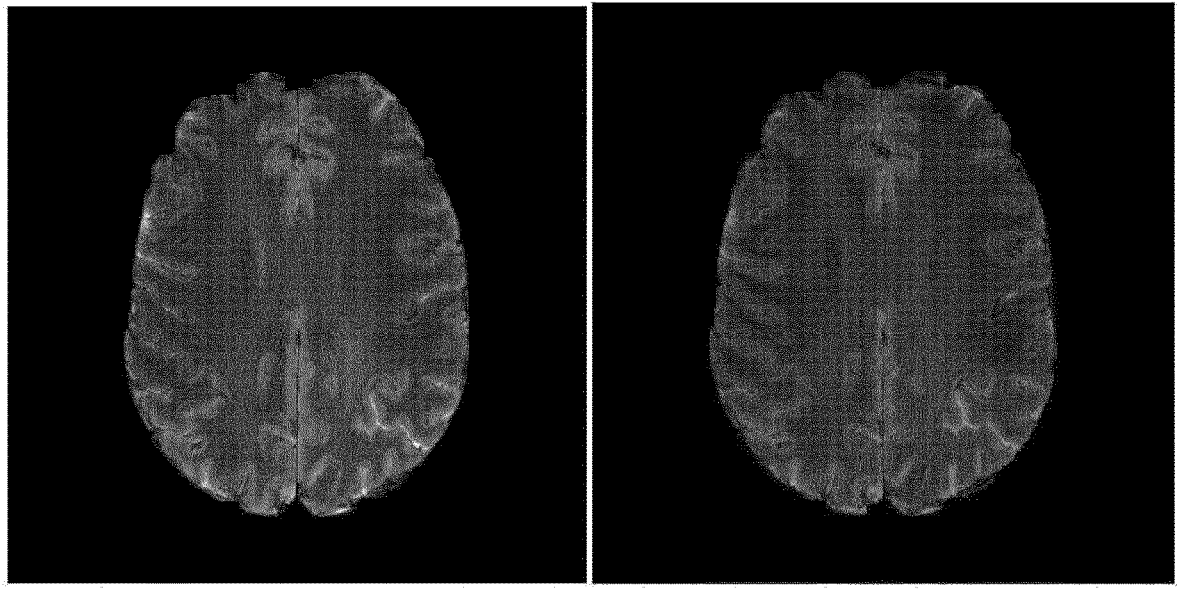
Fig. 10A
Fig. 10B
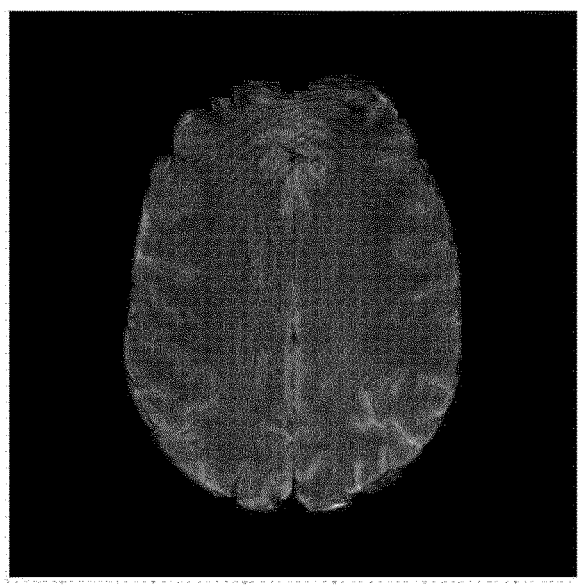
Fig. 10C

METHOD AND APPARATUS FOR ACCELERATED MAGNETIC RESONANCE IMAGING

CROSS-REFERENCE TO RELATED APPLICATIONS

This application is a National Stage of International patent application PCT/EP2018/074047, filed on Sep. 6, 2018, which claims priority to foreign European patent application No. EP 17306151.6, filed on Sep. 6, 2017, the disclosures of which are incorporated by reference in their entirety.

The invention relates to a method and apparatus for performing magnetic resonance imaging in a comparative short time. It mostly, but not uniquely, applies to the field of medical imaging.

Magnetic Resonance Imaging (MRI) is one of the most powerful imaging techniques used in clinical routine today, but remains a lengthy procedure, particularly when the acquisition of large and/or high resolution images, comprising several millions of pixels, is sought. For instance, acquiring a three-dimensional image of a human brain with a field of view of 205×205×52 mm$^3$ and a 200 µm resolution using a T2* sequence at an acceptable signal-to-noise ratio (SNR) of 7.6 may require an acquisition time of about three hours for a short repetition time (T1≅20 ms), which is clearly unacceptable for clinical purposes.

This is due to the fact that MRI images are obtained by sampling the so-called "k-space" domain, the spatial frequency spectrum of the image, which is related to the physical space by a multidimensional Fourier transform. Sampling theory teaches that the sampling frequency should be at least twice the highest frequency contained in the signal to be sampled (which, in the case of MRI, is the multidimensional Fourier transform of the body to be imaged), otherwise aliasing artifacts will appear; this is known as the Nyquist, or Nyquist-Shannon, criterion. As a consequence, using conventional acquisition schemes, the number of k-space samples must be at least equal to the number of pixels of the image to be reconstructed. Moreover, SNR requirements impose a minimum acquisition time for each sample.

Several techniques have been developed in order to reduce the acquisition time while avoiding artifact.

Some of these techniques, such as Simultaneous Multi-slice imaging (SMS) and parallel MRI involve the use of specialized hardware comprising multiple receiver coils for acquiring magnetic resonance signals. Their implementation is therefore expensive. Moreover, they provide a limited acceleration, because image quality drops fast with the acceleration factor. Even using both techniques simultaneously, the combined acceleration factor does not exceed 8 in practice.

Other techniques are compatible with the use of a single receiving coil (even though the use of multiple coils is also possible): this is the case of Partial Fourier imaging, which exploits redundancies in k-space information, non-Cartesian k-space filling such as radial or spiral and Compressed Sensing (CS). While Partial Fourier techniques only offer very limited acceleration factors (typically lower than two), Compressed Sensing allows order-of-magnitude accelerations especially while imaging with high matrix size (either high resolution and small field of view or low resolution and large field of view), see [Haldar, 2014].

A review of CS MRI can be found in [Lustig et al, 2008].

Compressed Sensing techniques rely on three principles:

The image to be reconstructed must admit a sparse (or compressible) representation. Said differently, it must be possible to decompose it on a predetermined basis (e.g. a wavelet basis) such that only a small fraction of the decomposition coefficients is non-zero for strict sparsity or significantly greater than zero for compressibility. Typically, in the case of a noisy signal, a coefficient is considered significantly greater than zero if its absolute value is at least equal to the noise standard deviation. Alternatively, only a predetermined fraction of the coefficients—those having the greatest absolute value—may be kept. For instance, only the top 1% of the coefficient may be kept, resulting in a compression factor of 100.

Reconstruction must be performed using a nonlinear method promoting sparsity of the image representation, as well as consistency with the acquired samples.

The k-space must be under-sampled, in order to accelerate the acquisition, following a pseudo-random pattern. The under-sampling reduces the number of signal acquisitions, and therefore provides the required acceleration, while pseudo-randomness ensures that, in the sparsifying representation, subsampling artifacts are incoherent, i.e. decorrelated or noise-like. This incoherence property is extremely important and measures the degree of correlation between any pair of elements taken in the sparsifying (e.g., wavelets) and sensing (e.g., Fourier in CS-MRI) bases.

Compressed sensing often uses non-Cartesian pseudo-random sampling of k-space since this strategy provides better incoherence (lower correlation between samples). However, a Cartesian sampling scheme has also been used originally since it was simpler to implement along the phase encoding direction (see [Haldar, 2011]). Moreover, the pseudo-random sampling should preferably be non-uniform, its density matching the energy distribution of the image to be acquired in the k-space. In clinical application, this usually means using a variable sampling density which is highest near the center of the k-space (low spatial frequencies) and decreases for high spatial frequencies.

From a purely theoretical point of view, the pseudo-random sampling could be obtained by drawing sampling points following a predefined probability distribution, corresponding to the required sampling density. But in practice this is not feasible except in the case disclosed in [Lustig et al, 2007], where sample locations where drawn independently according to Poisson disc sampling in the plane defined by the phase and partition encoding directions before collecting data values along straight lines orthogonal to that plane (readout direction). This, however, is a 3D approach, and cannot easily be applied to 2D (multi-slice) imaging. As a rule, in 2D MRI, samples are acquired along smooth trajectories which are defined by a time-varying magnetic field gradient applied to the body to be imaged after the excitation of its nuclear spins by a radio-frequency (RF) pulse.

Let represent the magnetic field gradient applied to the body to be imaged. This magnetic field gradient defines a trajectory in the k-space which is expressed by:

$$\vec{k}(t) = \gamma \cdot \int_0^t \vec{G}(\tau) d\tau \qquad (1)$$

Sampling is performed by acquiring the nuclear magnetic resonance (NMR) signal generated by excited nuclear spins at predetermined times, which correspond to points along said trajectory.

Both the gradient field amplitude $\|\vec{G(t)}\|$ and its slew rate cannot exceed respective limits Gmax and Smax, due to both hardware and, for clinical applications, physiological constraints. Therefore only sufficiently regular trajectories are allowed.

These trajectories may be bi-dimensional in 2D MRI, when only nuclear spins within a thin slice of the body are excited, on three-dimensional in 3D MRI techniques, where the excitation concerns the whole body or a thick slab thereof. In the following, for the sake of simplicity, only the case of 2D trajectories will be considered; the invention, however, also applies to 3D and even 4D (i.e. dynamic) MRI.

An important feature of MRI is that the NMR signal decays exponentially after the application of the exciting RF pulse, and typically vanishes. This limits the duration of signal acquisition, and therefore the length of each individual k-space trajectory. As a consequence, several excitation RF pulses, each followed by NMR signal acquisition along a respective trajectory, are required to perform a full k-space sampling. The repetition time TR of these excitation RF pulses—which imposes an upper limit on the duration of the signal acquisition—also depends on the used imaging technique, and in particular on the type of contrast which is sought (T1, T2, T2* . . . ).

Commonly used k-space trajectories are parallel lines (leading to Cartesian sampling), spokes (straight lines radially diverging from the center of the k-space), rosettes, uniform- and variable-density spirals. All of them have been applied to Compressed Sensing, for instance by performing only a limited number of signal acquisitions over a Cartesian grid or by randomly sampling spokes, spirals or rosettes.

Better results, however, are achieved by using "non-parametric" trajectories that provide larger incoherence:

Several authors have proposed to introduce random perturbations in "standard" (spokes, spiral . . . ) trajectories. See e.g. [Bilgin et al, 2008]; [Wang et al, 2012].

The paper [Chauffert et al, 2014] has proposed to randomly draw sampling points according to a desired probability distribution and to connect them by solving the Travelling Salesman Problem to obtain a continuous trajectory. A drawback of this approach is that continuity is not a sufficient condition (see above) for a 2D trajectory since each angular point requires stopping the gradients hence lengthening the acquisition duration.

The paper [Boyer et al, 2016] discloses an even more promising approach, based on the projection of the target sampling distribution onto the set of "admissible" 2D (or 3D) curves, i.e. to all the curves representing trajectories obtainable without exceeding the limits on the values of the magnetic field gradient and the corresponding slew rate. This method is called "SPARKLING", for "Segmented Projections Algorithm for K-space sampLING".

Sampling strategies alternative to "SPARKLING" are also disclosed in the literature, as detailed hereafter but none of them allows to simultaneously control the sampling density and the hardware trajectories to design physically plausible sampling schemes.

[Mir et al, 2004] and [Spiniak et al, 2005] disclose an algorithm for covering the whole k-space as fast as possible by relying on techniques used for missile guidance. This idea departs from "SPARKLING" trajectories since the aim was to satisfy Shannon's sampling theorem, meaning that the samples should cover the space uniformly.

[Curtis and Anand, 2008] teaches synthesizing random feasible trajectories using optimization techniques. The idea is to generate random control points uniformly distributed over the surface of a sphere. The method then comprises searching for a feasible trajectory that passes close to the control points using second order cone programming. Multiple random trajectories are generated this way, and a genetic algorithm selects the most relevant ones so as to ensure a uniform k-space coverage. This idea does not stem from a clear sampling theory and is based on randomness in contrast to "SPARKLING" trajectories. Moreover, this approach is specific to 3D imaging.

[Seeger et al, 2010], [Ravishankar and Bresler, 2011], [Liu et al, 2012] borrow ideas from statistical design for generating efficient sampling trajectories. [Seeger et al, 2010] teaches fixing a set of feasible trajectories (e.g. pieces of spirals) and selecting them iteratively by picking up the one that brings the largest amount of information at each step. Hence, finding the most meaningful trajectory becomes computationally intensive and incompatible with real-time acquisition. [Ravishankar and Bresler, 2011] and Liu et al, 2012] propose alternative approaches to reduce the computational burden by working on training images. These adaptive approaches suffer from a few drawbacks. First, the whole versatility of MRI scanners is not exploited since fixed trajectories are imposed. The SPARKLING formalism does not impose such a restriction. Second, even though adaptivity to the sampled image may seem appealing at first glance, it still seems unclear whether this learning step is really helpful [Arias-Castro et al, 2013]. Finally, these approaches strongly depart from existing sampling theories, whereas the SPARKLING trajectories are still motivated by solid and recently established theories.

A "non-parametric" trajectory may be defined as a trajectory that cannot be expressed as a function of a number of parameters lower than the number of k-space samples acquired along it. While a parametric trajectory has a fixed shape, along which samples are taken, the shape of a non-parametric trajectory is computed as a function of the required sampling density distribution, the above mentioned constraints, such as Gmax and Smax, and the number of samples. Additional constraints can be used to specify the echo time (time point at which the trajectory traverses the center of k-space). More generally, "affine constraints" can be used to define at which time the trajectory will pass through a specific k-space location.

The invention aims at further improving the performances of Compressed Sensing MRI using such non-parametric trajectories. "Improving the performances" means that the image quality—defined by suitable metrics of the similarity to a reference image acquired by a non-compressed method—is improved without lengthening the acquisition time, or equivalently that the acquisition time can be reduced without degrading the image quality.

The present invention achieves this aim by sampling the k-space in order to fulfill at least the Nyquist criterion in the central (low spatial frequency) part of the k-space, without increasing the readout time $T_{obs}$—i.e. the time during which the MR signal is acquired during each shot, which is often determined by the dynamic of the sequence and the prescribed weighting—in order to increase sampling efficiency. Ideally, the gradient raster time $\Delta t$ should take its minimal value compatible with hardware constraints of the MRI scanner and with physiological limits, e.g. 10 μs.

One key idea underlying the invention is to approach (as much as allowed by the hardware and physiological constraints) a randomized trajectory with controlled distance between the samples, in order to minimize aliasing artifacts. More precisely, the output sampling trajectory should resemble a blue noise sampling (often implemented in practice using Poisson-disk sampling) whose antialiasing properties and improved image rendering are well known [Nayak et al, 1998; Dippe and Wold, 1985]. In addition, avoiding large gaps between samples also improves the conditioning of the problem and decreases the noise in the context of parallel imaging [Vasanawala et al, 2011].

This approach can be used in various applications from uncompressed acquisitions to scenarii below the Nyquist sampling rate.

Hence, the proposed method is compatible with uniform sampling distributions, when the Nyquist criterion is met, and allows generating non-Cartesian trajectories which are more efficient than their Cartesian counterparts. On the other hand, the approach is also adapted to the CS framework (as mentioned earlier), since it also allows to generate variable-density trajectories for any arbitrary density.

An object of the present invention is then a method of performing magnetic resonance imaging of a body comprising the steps of:

a. immerging the body in a static and substantially uniform magnetic field, called longitudinal field oriented along a direction, called longitudinal direction;

b. transmitting to said body at least one radio-frequency pulse adapted for exciting nuclear spins inside said body;

c. after said or each said radio-frequency pulse, applying to said body a time-varying magnetic field gradient defining a non-parametric trajectory in a k-space and simultaneously acquiring samples of a magnetic resonance signal emitted by the excited nuclear spin, each sample corresponding to a point of the k-space belonging to said trajectory, wherein the points of the k-space corresponding to the samples define a pseudo-random sampling of the k-space, following a predetermined sampling density; and d. applying a sparsity-promoting nonlinear reconstruction algorithm to the acquired samples for reconstructing a magnetic resonance image of said body;

wherein, at least in a central region of the k-space, the distance between any two adjacent points belonging to a same trajectory is lower than 1/FOV, FOV being a size of a field of view of the reconstructed image of the object.

Another object of the invention is a magnetic resonance imaging apparatus (or "scanner") comprising:

a first coil suitable for generating a static magnetic field, called longitudinal field, substantially uniform within a volume of interest and oriented along a direction, called longitudinal direction;

a set of gradient coils suitable for generating, within said volume of interest, a time-varying magnetic field gradient;

at least one radio-frequency coils suitable for generating a radio-frequency pulse within said volume of interest; and a control unit configured or programmed to drive said gradient coils and said radio-frequency coil or coils, and to acquire and process signals received by said radio-frequency coil or coils, to carry out such a method.

Additional features and advantages of the present invention will become apparent from the subsequent description, taken in conjunction with the accompanying drawings, which show:

FIG. 1, the chronogram of a modified GRE (Gradient Recalled Echo) pulse sequence to play implementing a "SPARKLING" trajectory.

Figure 2:
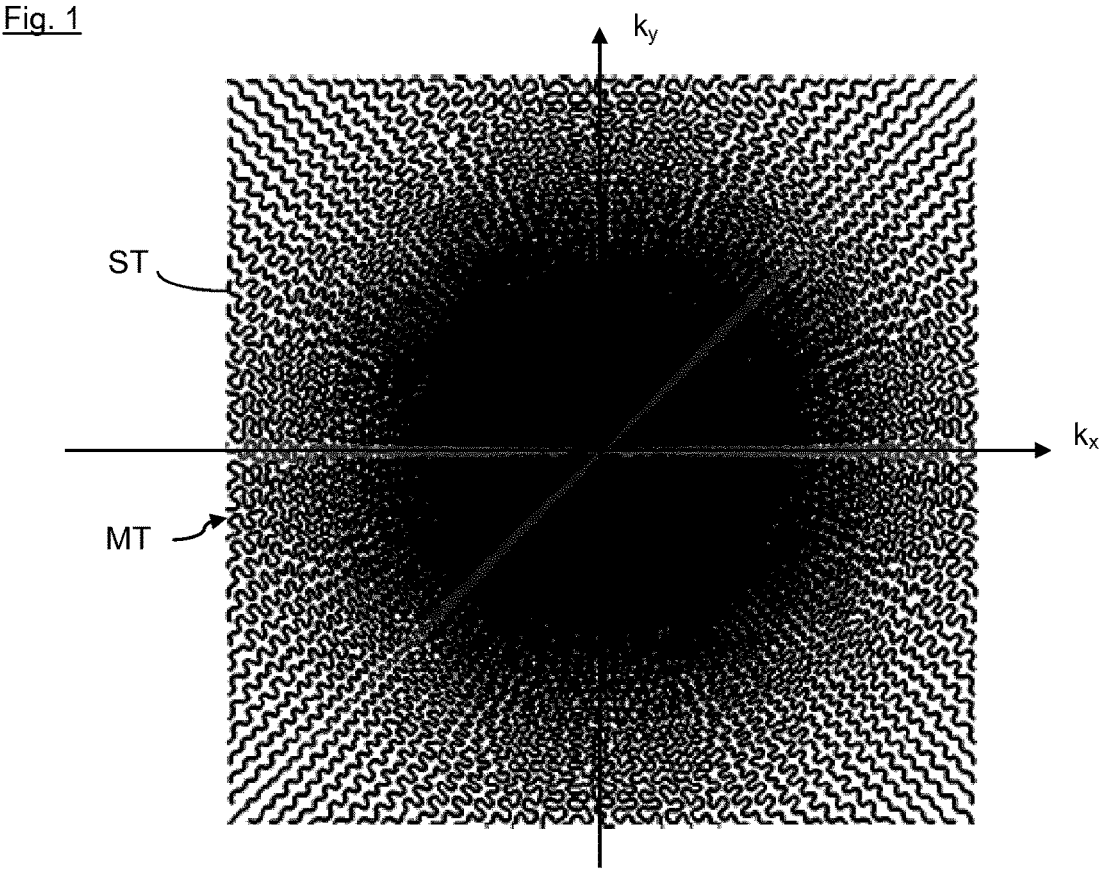

FIG. 2, a "SPARKLING" trajectory;

FIG. 3, a reference MRI image of a baboon brain, acquired ex vivo with a fully sampled Cartesian readout, used to assess the performances of the inventive method and reconstructed using FFT;

FIGS. 4A and 4B, plots of the distance $\Delta k$ between consecutive samples in trajectories according to the prior art and to an embodiment of the invention, respectively;

FIGS. 5A, 5B and 5C, "SPARKLING" trajectories with increasing numbers of samples per shot (and therefore decreasing gradient raster times), for a given number of shots.

Figure 11:
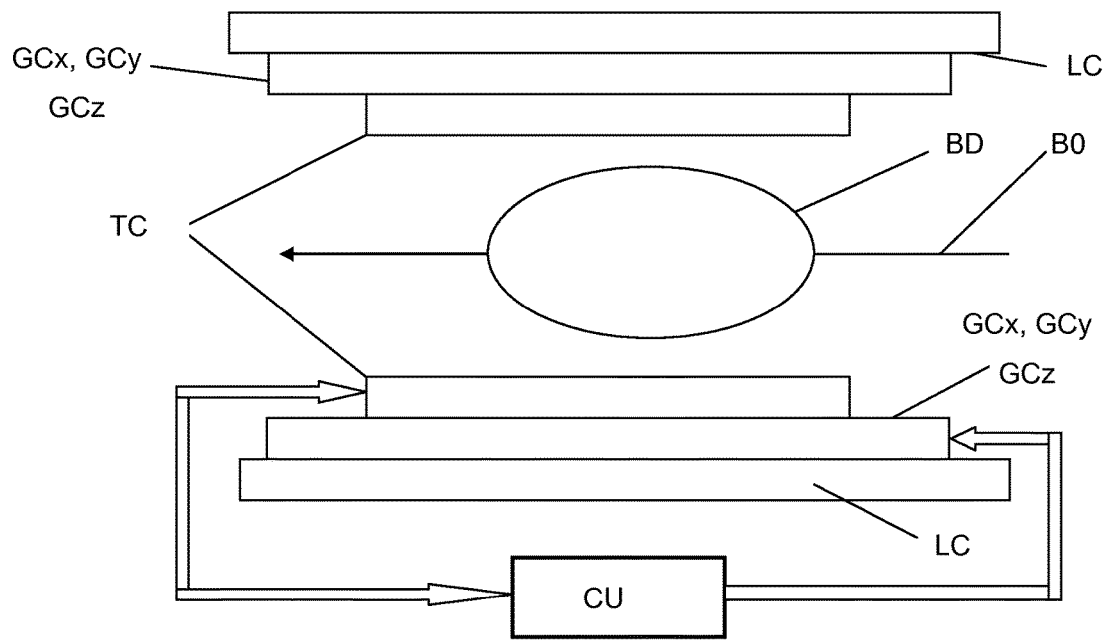
Figures 12A, 12B:
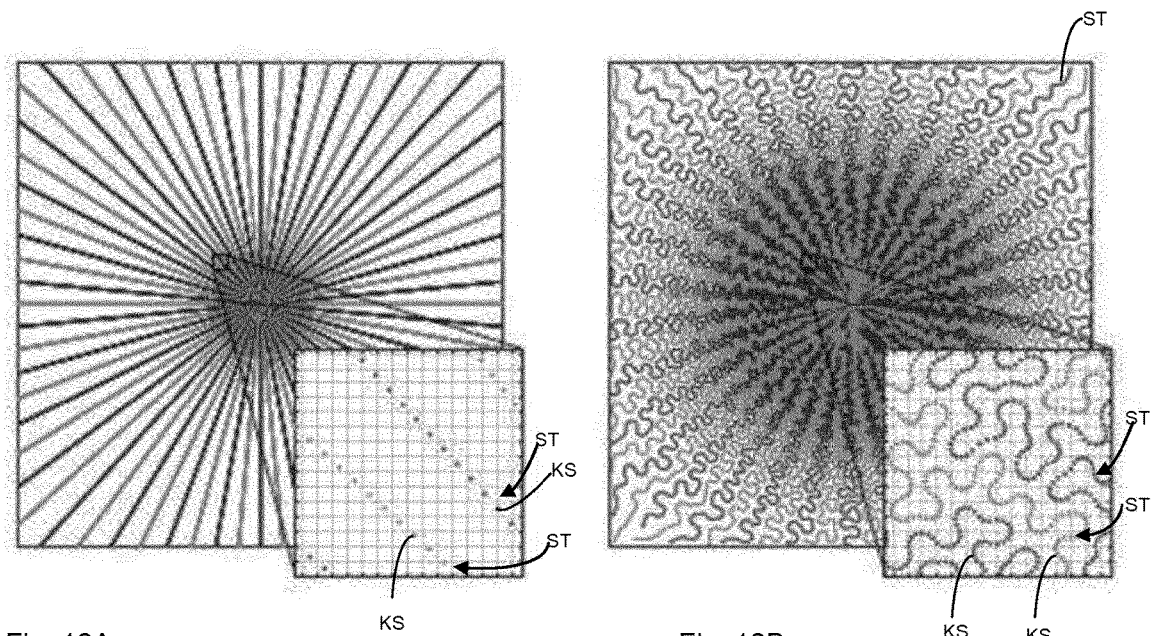
Figure 13A:
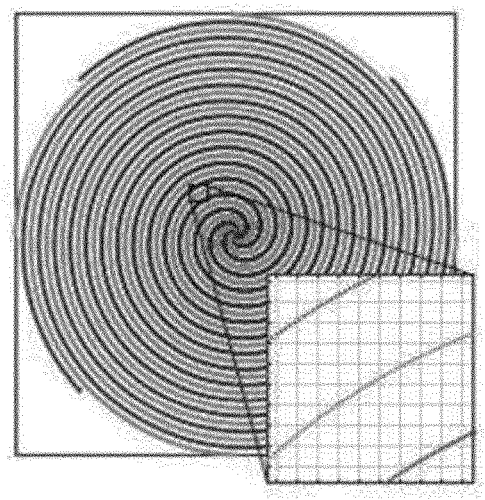
Figure 13B:
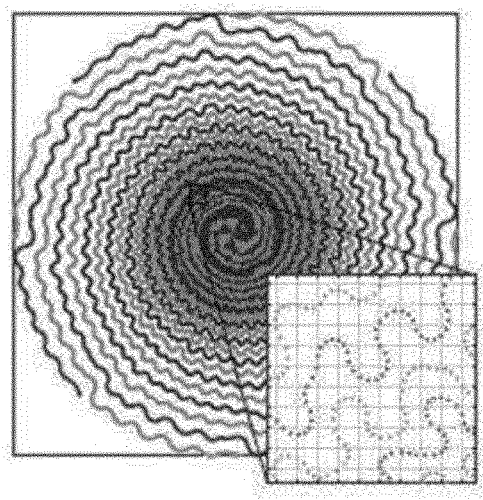
Figure 14A:
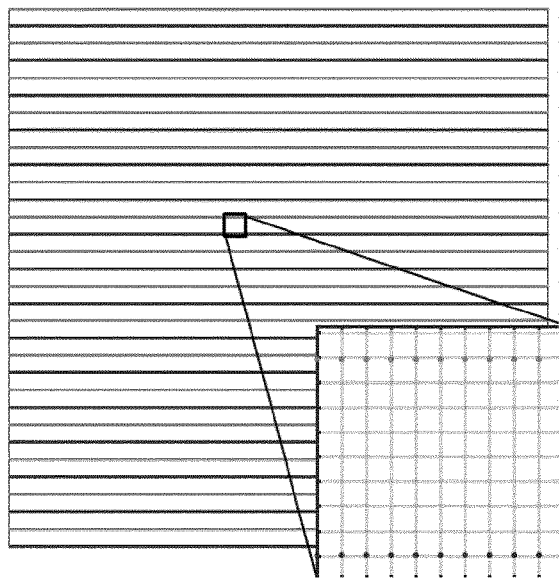
Figure 14B:
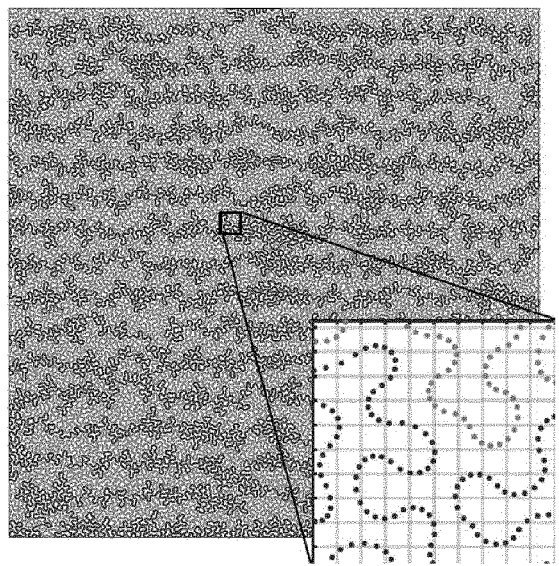
Figure 15:
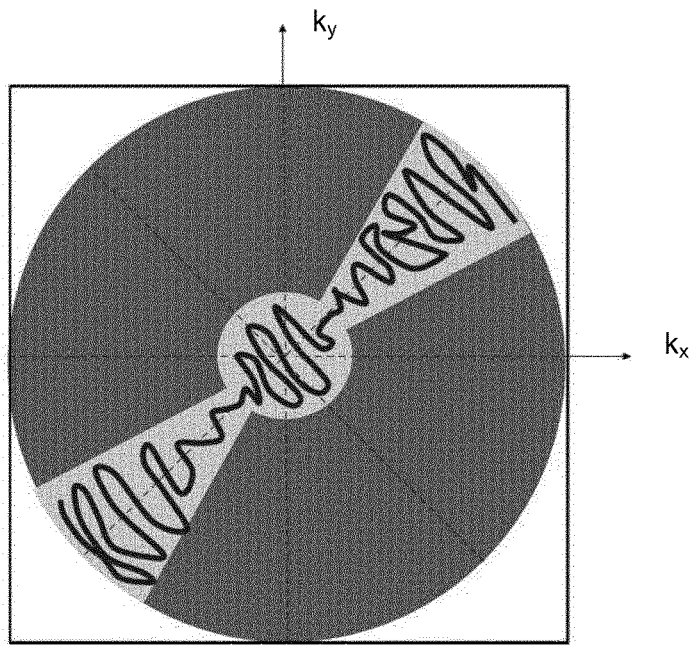
Figure 16:
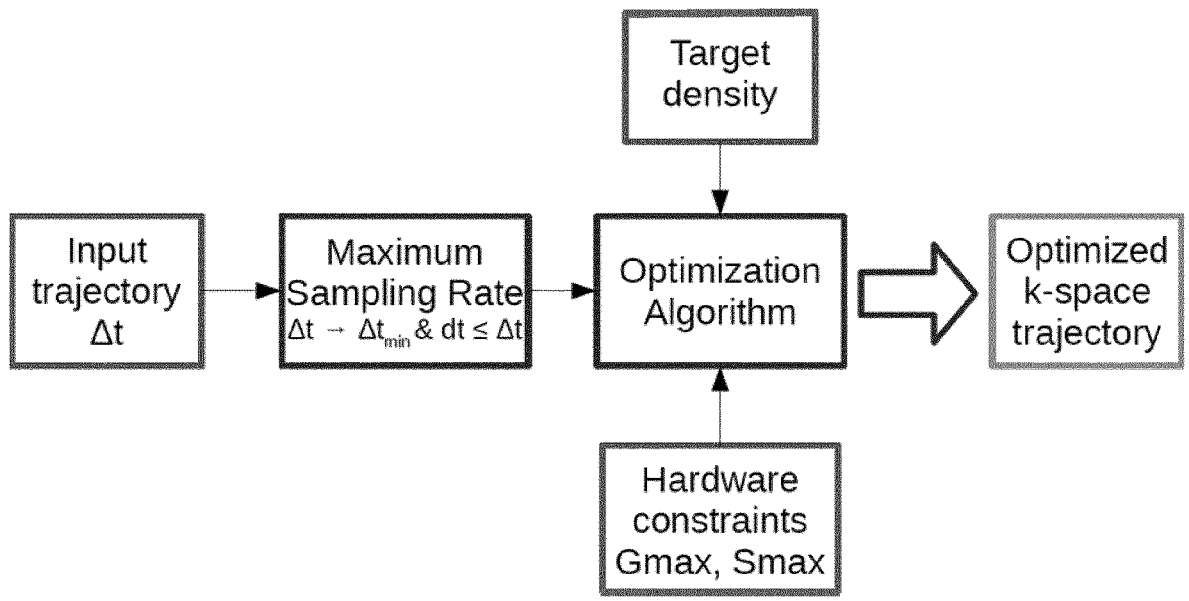
Figure 18:
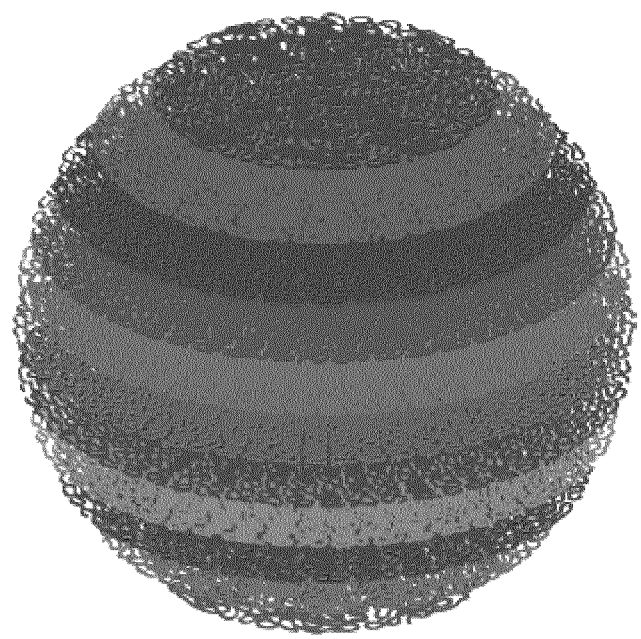
Figure 19:
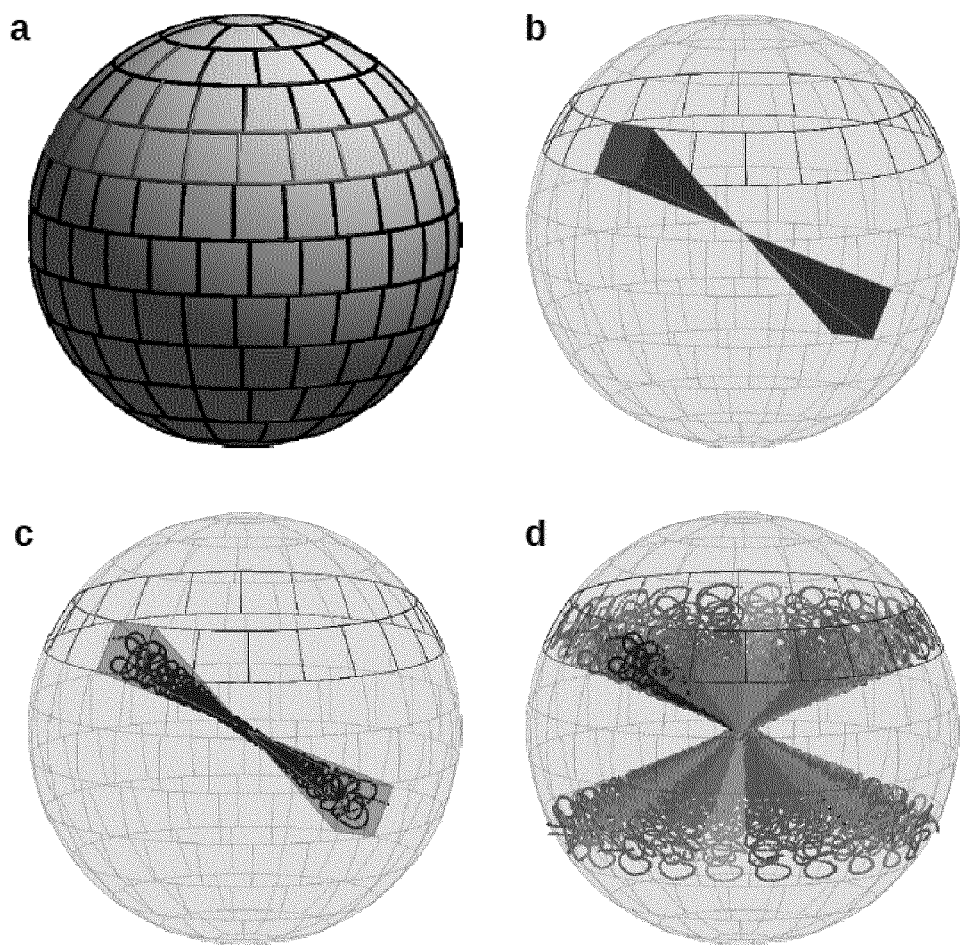
Figure 20:
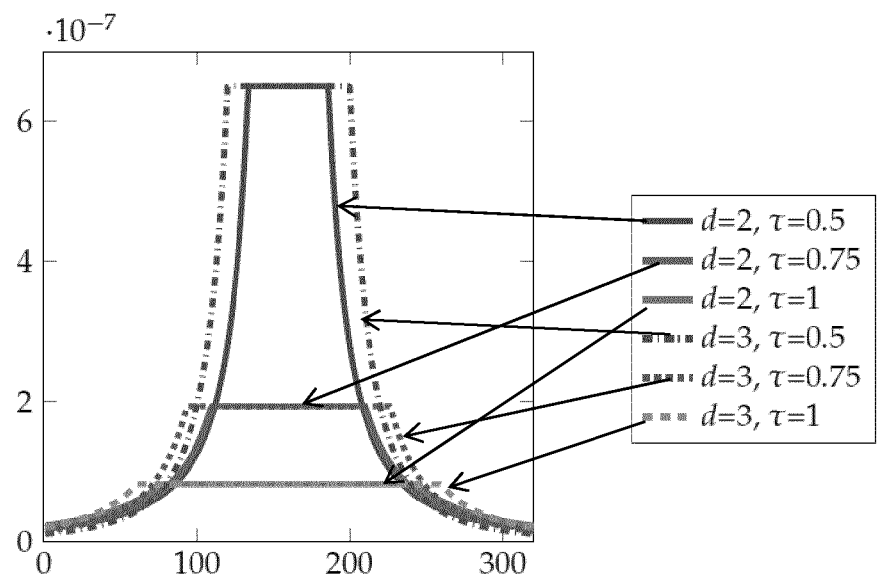

FIGS. 6A and 6B, MRI images illustrating technical results of the invention;

FIGS. 7A and 7B, plots illustrating quantitatively the gain in increasing the sampling rate up to a rate corresponding to the minimum achievable gradient raster time of the MRI scanner;

FIGS. 8A, 8B, 9A-C and 10 A-C, MRI images further illustrating technical results of the invention;

FIG. 11, a MRI apparatus suitable for carrying out a method according to the invention;

FIGS. 12A and 12B, a radial and a first "SPARKLING" sampling trajectory, respectively;

FIGS. 13A and 13B, a spiral and a second "SPARKLING" sampling trajectory, respectively;

FIGS. 14A and 14B, a Cartesian and a third "SPARKLING" sampling trajectory, respectively;

FIG. 15, a "PROPELLER" sampling scheme;

FIG. 16 a flow-chart of a method according to an embodiment of the invention;

FIGS. 17, 18 and 19A-D, three different sorts of 3D "SPARKLING" trajectories; and FIG. 20, a plot of different candidate target densities for designing 3D "SPARKLING" trajectories.

Different embodiments of the invention use different kinds of trajectories to perform a pseudo-random sampling of the k-space, with either a non-uniform or uniform sampling density. Hereafter, the particularly advantageous but non-limiting case of a "SPARKLING" trajectory will be considered in detail. "SPARKLING" are non-parametric trajectories, generated by an algorithm disclosed by [Boyer et al, 2016], initialized by a suitable parametric trajectory—e.g. radial, spiral or Cartesian—comprising a reduced number of shots compared with a "non compressed" trajectory. Indeed, the gain in sampling efficiency induced by "SPARKLING" patterns allows drastically reducing the number of acquired shots compared to parametric trajectories.

The shape of the resulting "SPARKLING" trajectory depends on the parametric trajectory used for initialization. In the following, the case of "SPARKLING" trajectories initialized by radial ones will be considered in detail.

For instance, FIG. 12A shows a 34-spoke radial trajectory and FIG. 12B a "SPARKLING" trajectory obtained using the radial trajectory of FIG. 12A for initialization. The "SPARKLING" trajectory consists of a set of $N_c=34$ elementary trajectories ST, one for each spoke of the initializing trajectory. Individual k-space sampling points, some of which are designated by reference KS, are visible in the inserts of the two figures. As discussed above, and as clearly visible on the figures, the "SPARKLING" trajectory is more densely sampled than the initializing one. Its "winding" shape ensures a more efficient exploration of the k-space.

Similarly, FIG. 13A shows a spiral sampling trajectory and FIG. 13B a corresponding "SPARKLING" one.

Also, FIG. 14A shows a Cartesian sampling trajectory and FIG. 14B a corresponding "SPARKLING" one. The insert of FIG. 14A clearly shows that the Cartesian trajectory is under-sampled in one direction of the k-space by only taking one eighth of the number of elementary (horizontal) trajectories which would be required to perform a full sampling satisfying the Nyquist criterion, but each elementary trajectory ST is sampled at the Nyquist rate.

FIG. 1 shows the chronogram of a pulse sequence—more particularly a Gradient Recalled Echo (GRE) sequence for T2* weighted anatomical imaging—implementing a "SPARKLING" k-space trajectory according to an embodiment of the invention. It is supposed that a body to be imaged (e.g. the head of a patient) is immerged in a static and homogeneous magnetic field B0 oriented along a "longitudinal" direction z. This magnetic field induces a partial alignment of the spins of the atomic nuclei of the body. The aligned nuclear spins may be excited (i.e. flipped) by a radio-frequency pulse RFP at a suitable frequency (Larmor frequency), depending on the values of the magnetic field B0 and of the magnetic momentum of the nuclei. In 2D sequences, as the one illustrated on the figure, a magnetic field gradient $G_z$—i.e. a magnetic field oriented along the z direction, whose magnitude varies linearly along this same direction—is also applied. This has the effect of making the Larmor frequency variable along z; as a consequence, only the nuclear spins within a thin slice of the body are resonant with the RF pulse and can be excited. As known in the art of MRI, this "slice selection" gradient pulse is followed by a short negative blip of the $G_z$ magnetic field gradient ("refocusing gradient") which compensates for a dispersion of the nuclear spin orientations in the xy plane, perpendicular to the z direction.

Due to the use of a slice selection gradient $G_z$, only a 2D image of the selected slice of the body is acquired, which requires sampling of a 2D $k_x k_y$ plane of the k-space; in the following, the expression "k-space" will be used to designate both the three-dimensional $k_x k_y k_z$ space and a two-dimensional plane within it. A trajectory in the k-space (more precisely, in the 2D $k_x k_y$ plane) is defined by playing $G_x$ and $G_y$ gradients after the end of the RF excitation pulse. It is important to underline that the applied magnetic field is always oriented along the z direction, but its magnitude shows linear variations along the x and y directions. First of all, $G_x$ and $G_y$ pulses are applied to reach a suitable point on the boundary of the region of the $k_x k_y$ plane to be sampled. Then "arbitrary" $G_x$ and $G_y$ waveforms are played, defining a winding trajectory with an overall radial orientation, directed toward the center of the $k_x k_y$ plane. Simultaneously, samples of the NMR signal emitted by the excited nuclei are acquired by one or more radio-frequency coil connected to a suitable acquisition circuit including an analog-to-digital (ADC) converter. The acquisition period, whose duration $T_{obs}$ is limited by the decay of the NMR signal, is designated by reference OP on FIG. 1. After the end of the acquisition period, a final $G_x$ gradient pulse ("spoiling gradient") is applied to cancel residual transversal magnetization. The repetition time TR corresponds to the interval beginning just before the radio-frequency pulse RFP and ending at the end of the spoiling gradient pulse.

This sequence is repeated several times with different $G_x$ and $G_y$ waveforms defining respective k-space trajectories which, together, provide the required k-space sampling. The ensemble constituted by an excitation RF pulse and the associated gradient waveforms is called a "shot"; each shot corresponds to an elementary trajectory (cf. elements ST on FIG. 12B), and the acquisition of an image of a selected slice of the object usually requires several shots. FIG. 2 shows a set of $N_c$=0.60 "SPARKLING" trajectories or spokes, inhomogeneously sampling the $k_x k_y$ plane. On this figure, reference ST designate an individual trajectory, corresponding to a "shot", and MT to the overall multi-shot trajectory, comprising the $N_c$ individual trajectories.

In practice, the magnetic field gradients $G_x$ and $G_y$ undergo stepwise changes at discrete time-points separated by intervals of duration Δt ("gradient raster time"). Sampling is also performed at regular intervals of duration dt ("ADC dwell time"). According to an embodiment of the invention, the ADC dwell time dt is preferably lower than, or at most equal to, the gradient raster tile (dt≤Δt) so as to allow collecting several samples between two consecutive gradient steps. At the same time, reducing the ADC dwell time beyond a certain limit decreases the SNR to an unacceptable level. Therefore, for each specific embodiment of the invention there is an optimal value for dt which can be found.

Let $k_i(1)$ the position, in the k-space, of the starting point of the trajectory associated to the $i^{th}$ shot. A first sample of the NMR signal is acquired in correspondence to this point. The other samples correspond to k-space positions given by:

$$k_i(m) = k_i(1) + \gamma \left( \sum_{j=1}^{q} G_i(j) * \Delta t + G_i(q+1) * r \right) \quad (2)$$

where m∈[2:M] is an integer index, M being the overall number of samples acquired along the trajectory, and q and are respectively the modulus and the rest of the Euclidean division of the acquisition time by:

$$t_{ADC,m} = (m-1)*dt = q*\Delta t + r \quad (3)$$

If dt=Δt, then r=0 and the number of ADC samples matches the number of gradient time steps. If dt<Δt, then the number of ADC samples is larger than the number of gradient time steps.

FIG. 3 shows a 512×512 pixel MRI image of a slice of a baboon brain, acquired using a conventional "Cartesian" readout—i.e. straight-line k-space trajectories and a regular sampling of the $k_x k_y$ plane following a rectangular grid. More precisely, the image has been acquired using 512 shots with 512 samples per shot. The number of samples in the k-space is equal to the number of pixels in the reconstructed image, satisfying the Nyquist criterion. The acquisition time window for each shot had a duration $T_{obs}$=30.72 ms, and the overall scanning time was $T_f$=4 minutes 42 seconds. In the following, the image of FIG. 3 will serve as a reference for assessing the performances of such methods.

In "conventional" MRI methods, i.e. non-accelerated ones using a full Cartesian readout, the number of shots $N_f$ is usually taken equal to the number of pixels of the image to be reconstructed along, say, the y direction: $N_f = n_y$. More generally, in case of a non-Cartesian (e.g. radial) readout, $N_f = \sqrt{N}$, where $N = n_x \cdot n_y$, $n_x$ being the number of pixels along the x direction. The acquisition time $T_f$ is given by $T_f = N_f TR$, where TR is the shot repetition time, i.e. the interval between two successive RF pulses, which—as mentioned above, depends on the sought contrast, and therefore on the specific pulse sequence used.

In multi-shot Compressed Sensing MRI, only a reduced number of shots is used: $N_c = \alpha N_f$ with α<1. Usually, the number $n_s$ of samples is the same as in the case of full acquisition ($n_s=n_x$). The repetition time TR is bounded by the relaxation time of nuclear spins, therefore is unaffected by the readout method. Therefore, the acquisition time is $T_c=N_c TR$.

If R refers to the reduction factor—i.e. the factor by which the number of acquired samples is reduced—and A the acceleration factor—i.e. the factor by which the acquisition time is reduced, one finds:

$$R=N_f/N_c=\alpha^{-1}; A=T_f/T_c=N_f/N_c=\alpha^{-1} \quad (4)$$

and therefore A=R.

As mentioned above, an idea of the present invention consists of improving the k-space sampling efficiency—which requires increasing the number of acquired samples, and therefore reducing the reduction factor R, which can even become lower than 1—without any supplementary cost in terms of acquisition time, i.e. with fixed A. As explained above, the acquisition time is the product of the number of shots, $N_c$, and the repetition time TR. As the repetition time is determined by the particular MRI sequence used, an accelerated acquisition (A>1) can only be obtained if the number N, of shots is lower—and preferably significantly lower, i.e. by at least a factor of 5 or, better, 10—than the number of pixels of the target image along one dimension, e.g. $N_c < n_y$. Reducing R requires acquiring, along each elementary trajectory, a number of k-space samples which is higher than the number of pixels of the target image along the other dimension: $n_s > n_x$. Otherwise stated, according to the invention, a reduced number of shots is used, but the k-space trajectory corresponding to each shot is "oversampled". It is important to stress that, in the inventive method, the individual single-shot trajectories are oversampled, but the k-space as a whole is not necessarily so. Indeed, according to different embodiments of the invention, the reduction factor R may be greater than, equal to or lower than 1.

Importantly, the oversampling must be performed in such a way that, at least in a central region of the k-space (i.e. for "low" spatial frequencies) the maximal k-space distance between consecutive samples is such that $\Delta k < \Delta k_{cart}$ where $\Delta k_{cart}=1/FOV$, FOV being the field of view of the image to be reconstructed (defined as its size along one dimension, preferably the smallest one if the image is not square).

The repetition time is fixed, determined by NMR weighting considerations, and so is the acquisition time available for each shot. As a consequence, oversampling a trajectory implies reducing the acquisition time for each k-space sample, and therefore its SNR. This is the main reason for which such an oversampling strategy has not been considered before, to the best knowledge of the inventors.

Indeed, as it will be discussed further, in particular with reference to FIGS. 6A/6B and 7A/7B, oversampling is not beneficial—and may even be detrimental—when conventional "parametric" k-space trajectories. The inventive sampling approach is only advantageous in the case of "non-parametric" trajectories, such as "SPARKLING" ones.

Indeed, if one sticks to the given support of any parameterized trajectory (e.g., radial, spiral, rosette . . . ), oversampling along this curve basically consists of collecting more Fourier samples (with $dt < \Delta t$) over a fixed trajectory (i.e., increasing $n_s$). However, the support trajectory being fixed and parameterized, this does not offer the opportunity to explore a larger or different portion of k-space. As a consequence, there is no gain in collecting more information over a given trajectory in terms of image quality.

The situation is different when a non-parametric trajectory is used, whose support changes when the number of samples per shot is increased (i.e. when $\Delta t$ is decreased), thus offering the possibility to collect information over a wider portion of k-space. This is particularly true when the trajectory is based on an optimization algorithm whose goal is to maximize the coverage of collected Fourier samples in a minimum amount of time, as in the case of "SPARKLING".

"SPARKLING" relies on an optimization-based method that consists of projecting a target sampling distribution over a set of discrete pushforward measures, in particular supported by smooth trajectories [Lazarus et al, 2017; Boyer et al, 2016]. Mathematically, this problem can be cast as a non-convex variational optimization problem under possibly non-convex constraints [Boyer et al, 2016]. The constraints are typical expressed by maximal acceptable values for the gradient amplitude and slew rate, but additional affine constraints may also be used—e.g. imposing that the trajectory passes through a particular point of the k-space at a defined time point (e.g, for echo time definition).

The "SPARKLING" trajectories of FIG. 2, given for illustration purposes only, are the projection of a radial 2D density, decaying with a power of 2, onto measures carried by trajectories that fulfill the constraints involved in MRI sampling, namely the gradient amplitude and slew rate: Gmax=40 mT/m and Smax=200 T/m/s. The $N_c$=60 trajectories of FIG. 2 comprise $n_s$=4096 sampling points and the samples are used to reconstruct a 512×512 image of a baboon brain, to be compared with the reference image of FIG. 3. This means that each trajectory is oversampled by a factor of 8. The reduction factor R is very close to one (R≅1.067)—otherwise stated, the overall number of samples is almost identical to that which would be acquired in a conventional Cartesian readout satisfying the Nyquist condition.

The acceleration factor A, however, is very high: A=512/60=R≅8.53, which means that the acquisition time is reduced by almost one order of magnitude. This is made possible by the fact that the acquisition time for each trajectory, or "observation time" $T_{obs}$, is not affected by the number of samples $n_s$, the increase in the number of samples being obtained via a corresponding reduction of the sampling time dt. Here, $T_{obs}$=30.72 ms ($\Delta t$=10 μs, $T_{obs}$=6×512×$\Delta t$, where 6 is the oversampling factor) and dt=7.5 μs.

In an exemplary embodiment of the invention, reconstruction was performed using an iterative and nonlinear (sparsity promoting) method, based on the minimization of the following LASSO criterion:

$$\min_z \|Az-y\|_2^2 + \lambda \|z\|_1 \quad (5)$$

where A=ΩF Ψ with Ω the sampling mask, F the non-uniform Fourier transform, and Ψ a sparsifying transform (e.g., wavelet or curvelet transform, here a wavelet transform using Daubechies wavelets on 4 resolution levels). The data is represented in a vectorized manner by y and the image to be reconstructed reads: x=Ψ z where z is the sparse representation of x in the Ψ basis. Parameter λ is the regularization parameter that performs the balance between the data consistency term ($L_2$ norm) and the sparsity promoting prior ($L_1$ norm) and was set manually to maximize any given image quality criterion (e.g., 1/NRMSE or SSIM, see FIGS. 7A and 7B). For minimization purposes, a proximal optimization method, namely FISTA—for Fast Iterative Soft Thresholding Algorithm [Beck and Teboulle, 2009], was used.

"Regridding" algorithms that perform interpolation in the Fourier domain before applying a Fast Fourier Transform were also tested for image reconstruction. As discussed below, with reference to FIGS. 7A and 7B, they turn out to be significantly less performing than proximal method such as FISTA.

FIG. 4A is a plot of the distance Δk between consecutive samples in a prior art "SPARKLING" Compressed Sensing trajectory used to acquire a 512×512 pixel image. The full trajectory comprises $N_c$=60 elementary (single-shot) trajectories, each including 512 k-space samples. FIG. 4B is a similar plot, but for a "SPARKLING" trajectory according to the invention, wherein $N_c$ and the observation time are unchanged, but the sampling rate along each elementary trajectory is increased by a factor of 4 ($n_s$=2048).

In the original version of the "SPARKLING" trajectories ([Boyer et al, 2016]), the Nyquist constraint was not managed as shown in FIG. 4A, whereas in the most recent one, the Delta k value is kept lower than the Cartesian value, as illustrated in FIG. 4B (note the scale difference). On these figure, lines of different shades of gray correspond to different segments of the sampling trajectory. These figures clearly demonstrate that oversampling reduces the local Δk which gets closer or under the $Δk_{cart}$ line, not necessarily everywhere, but at least for an oversampling factor of 4. Center and borders of k-space are most concerned and increasing the oversampling factor may still allow meeting this constraint.

The constraint $Δk≤Δk_{cart}$, at least in a central part of the k-space was therefore added to the existing ones in the projection algorithm of a given radial density onto a set of smooth measures, which already involved hardware gradient constraints (Gmax=40 mT/m and Smax=200 T/m/s) and TE selection (the time point at which the center of k-space is traversed k(TE)=0).

FIGS. 5A, 5B and 5C show "SPARKLING" trajectories $MT_1$, $MT_2$, $MT_3$ for increasing numbers of samples over a same region of the k-space: $n_s$=1024, 1536 and 2048 respectively. It can be seen that as the number of samples per shot increases, the set of segments which is solution to the projection problem ("SPARKLING" trajectory) becomes more organized and shots get a more symmetric configuration. This is a direct consequence of decreasing Δt from 30 μs (FIG. 5A) to 15 μs (FIG. 5C). For Δt=15 μs ($n_s$=2048), each shot uses all the length available to spread while in the case of Δt=30 μs ($n_s$=1024) there are adjacent segments of very different extent. That justifies the positive effect of oversampling. The lowest possible gradient raster time, for the MRI scanner used to test the inventive method, corresponds to Δt=10 μs, yielding $n_s$=3072. Up to this value (so for panels in FIG. 5A-C), dt has been chosen equal to Δt. Going beyond this value requires selecting dt<Δt as in the case of ns=4096.

Of course, increasing the number of shots N, has a positive effect too but at the expense of the increase of the scanning time.

An important question is whether it is beneficial or not to push the oversampling factor beyond the value of 4 considered above. This aspect was first investigated in retrospective CS experiments before being analyzed in prospective scenarios.

In Table 1, SSIM—a classic image quality assessment score [Wang et al 2004]—is computed as a function of the number of shots ($N_e$) and the number of samples ($n_s$), up to $n_s$=3072, which corresponds to an ADC dwell time dt=1 μs, the lowest value achievable for the hardware used by the inventors.

TABLE 1

|  | $n_s$ = 1024 | $n_s$ = 1536 | $n_s$ = 2048 | $n_s$ = 3072 |
| --- | --- | --- | --- | --- |
| $N_c$ = 40 | 0.702 | 0.812 | 0.87 | 0.911 |
| $N_c$ = 50 | 0.759 | 0.847 | 0.897 | 0.94 |
| $N_c$ = 60 | 0.794 | 0.87 | 0.918 | 0.957 |
| $N_c$ = 80 | 0.839 | 0.905 | 0.949 | 0.98 |

Table 1 shows that SSIM continuously increases up to $n_s$=3072 (and possibly beyond), and that increasing permits to get high SSIM values faster (i.e. at constant scanning time) than increasing the number of shots N, for a given $n_s$.

As regards the prospective comparison, the "SPARKLING" trajectory was compared to radial spokes reaching the corners of the sampled k-space region to demonstrate that oversampling over shots has a positive effect in the former situation and none in the second one. In both cases, the number of shots was set to N, =60 corresponding to A=8.5 for N=512×512, and $n_s$=4096 (or dt=7.5 μs<Δt=10 μs), so that R=1.06.

The results of the prospective comparison are shown on FIGS. 6A ("SPARKLING" trajectories) and 6B (RADIAL ones) for the above mentioned setting of N, and $n_s$. Visual inspection of FIGS. 6A and 6B allows to conclude that MR images reconstructed from accelerated "SPARKLING" trajectory(s) are of better quality (details and contours are better preserved) than those originating from radial-based sampling with the same acceleration factor (for instance, in the latter case cortical sulci are over-smoothed).

Beyond this specific example, the parameter $n_s$ was swept for both "SPARKLING" and radial trajectories to see which limit can be reached without degrading MR image quality as compared to the Cartesian reference. The results are reported in terms of SSIM on FIG. 7A, and of normalized residual mean squared error (NRMSE) on FIG. 7B. On these figures:

line SF represent the SSIM of the images obtained using "SPARKLING" trajectories and FISTA reconstruction;

line SF' represent the NRMSE of the images obtained using "SPARKLING" trajectories and FISTA reconstruction;

line SR represent the SSIM of the images obtained using "SPARKLING" trajectories and "regridding" reconstruction;

line SR' represent the NRMSE of the images obtained using "SPARKLING" trajectories and "regridding" reconstruction;

line RF represent the SSIM of the images obtained using radial trajectories and FISTA reconstruction;

line RF' represent the NRMSE of the images obtained using radial trajectories and FISTA reconstruction;

line RR represent the SSIM of the images obtained using radial trajectories and "regridding" reconstruction;

line RR' represent the NRME of the images obtained using radial trajectories and "regridding" reconstruction.

It can be seen that SSIM increases up to $n_s$=4096 (with a plateau achieved at $n_s$=3072 for SSIM) for "SPARKLING" trajectories, whereas oversampling had no positive impact on radial trajectories. Similarly, NRMSE decreased down to a minimum achieved at $n_s$=4096 for "SPARKLING" trajectories.

Similar conclusions could be drawn when comparing radial spokes with other optimization-based trajectories in which the sampling path evolves as a function of $n_s$ or when comparing "SPARKLING" with alternative parameterized non-Cartesian curve such as spirals.

Similar results hold when fewer shots are used i.e. for more accelerated acquisitions and thus more under-sampled sampling schemes. For instance, FIGS. 8A and 8B correspond to A=15 ($N_c$=34)/R=1.88 ($n_s$=4096). These images confirm that "SPARKLING" trajectories designed for CS (i.e. with variable density) and using a maximum degree of freedom offered by a minimum gradient raster time outperform radial trajectories for any sampling rate. The sampling trajectories are similar to those of FIGS. 12A, 12B except for the different number of shots.

Beyond this ex-vivo validation, in vivo acquisitions with single and multiple channel coils have been performed using "SPARKLING" and radial are consistent with the ex-vivo findings. In what follows, only reconstructed MR images from multiple (32) channel coils acquisition are reported NEX >1. For multiple channel coils acquisition, the reconstruction criterion (5) becomes $$\min_z \sum_{l=1}^{L} \|\Omega F\ S_l \Psi z - y_l\|_2^2 + \lambda \|z\|_1 \quad (6)$$

where $y_l$ is the data collected on the lth coil and $S_l$ the corresponding sensitivity matrix, which was estimated from the center of k-space.

Figure 9C:
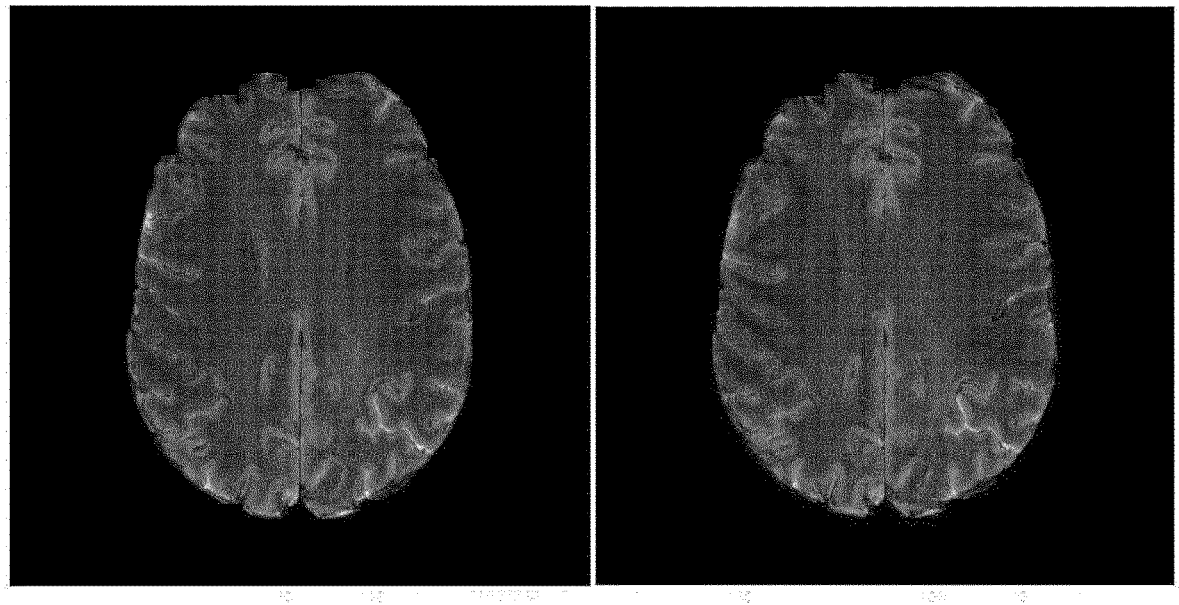
Figure 9C:
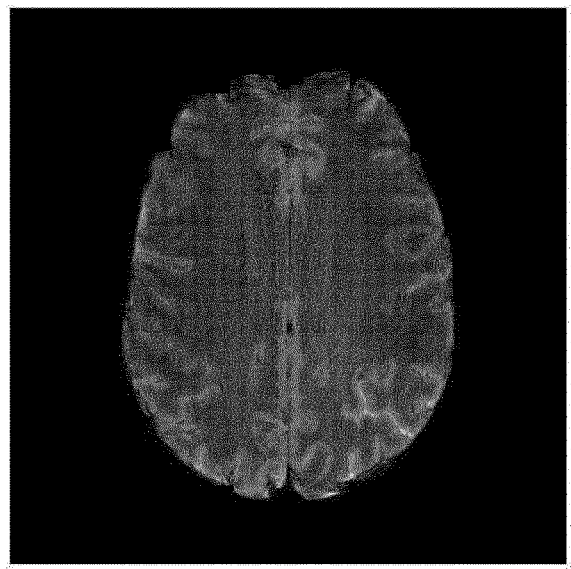

In FIGS. 9B and 9C, respectively, in-vivo prospective results, obtained using a "SPARKLING" sampling scheme according to the invention and a "conventional" radial one, respectively, are shown for A=8 in a human brain and compared to the Cartesian reference image 9A. The acquisition time is 35 s for both the "SPARKLING" and the radial sampling scheme, and 4 m 42 s for the reference image (obtained using a Cartesian scheme) of FIG. 9C. The sampling trajectories are similar to those of FIGS. 12A, 12B except for the different number of shots.

Similarly, for the same participant, in FIGS. 10A-C the same prospective comparison between "SPARKLING" (FIG. 10B) and radial-based (FIG. 10C) sampling schemes was carried out for A=15, as well as the comparison to the Cartesian reference image (FIG. 15A). In both cases (A=8 and A=15), the MR reconstructed from radial based sampling suffers from severe artifacts (stripes) that destroy the image structures located at the front of the brain. This effect is more pronounced for A=15.

The sampling trajectories are similar to those of FIGS. 12A, 12B except for the different number of shots.

FIG. 11 illustrates, very schematically, an apparatus for carrying out a method according to the invention. This apparatus is basically a MRI scanner comprising a longitudinal coil LC for generating the longitudinal field B0, a single or preferably a plurality of radio-frequency coils TC for generating RF pulses and receiving the NMR signal, three gradient coils GCx, GCy and GCz for generating magnetic field gradients $G_x$, $G_y$, $G_z$ along the x, y and z axes respectively (not represented). The gradient coils are disposed around a volume in which a body BD to be imaged can be introduced. The term "body" should be construed broadly, designating any living or non living object containing atomic nuclei at least some of which are supposed to have nonzero spin. For instance, body BD may be a human or animal body or a portion thereof (e.g. a head) or an article of manufacture such as a "phantom". The apparatus also comprises a control unit CU for driving said gradient coils in and said radio-frequency coil or coils according to a predetermined excitation and readout sequence (see e.g. FIG. 1) and for acquiring NMR signals from the radio-frequency coil or coils and performing image reconstruction. The control unit may include a suitably programmed general purpose computer or digital signal processor, suitably configured specialized digital circuits or both. It also includes a receiving circuit for acquiring NMR signals, comprising a signal amplifier, a sampler and an analog to digital (ADC) converter.

The invention has been described with reference to specific examples, based on high-resolution (N=512×512), two-dimensional T2* imaging with GRE sequences. More particularly, experimental data (prospective ex-vivo and in-vivo acquisitions) were acquired on a 7 Tesla scanner using single channel and multiple channel receiver coils with the following acquisition parameters: repetition time: TR=550 ms, echo time TE=30 ms, spin flip angle α=25°, observation time $T_{obs}$=30.72 ms, 3072 samples per shot (dt=10 μs). However, the scope of the invention is not limited to this specific case.

Indeed, the invention may be used to replace and improve any MRI sampling scheme. As shown on the flow-chart of FIG. 16, a method according to an embodiment of the invention takes as its inputs an initializing k-space trajectory, characterized by a gradient raster time Δt, a target sampling density and hardware constraints such as a maximum gradient value (Gmax) and/or a maximum gradient slew rate value (Smax). The input trajectory is then oversampled by reducing the gradient raster time Δt, ideally down to a minimum possible value $\Delta t_{min}$, and by taking an ADC dwell time dt≤Δt. An optimization algorithm, e.g. of the kind described in [Boyer et al, 2016] (projected gradient descent) is then carried out, which results in modifying the oversampled initializing trajectory in order to approximate the target density while complying with the hardware constraints.

The invention applies to 2D multislice k-space sampling, as described, but also to 3D imaging and even 4D imaging where acceleration can be largely increased. Trajectory optimization can be initialized starting from any classic k-space filling support (including Cartesian lines, spirals, radial, . . . ).

The inventive method may be adapted to any types of MR readout scheme segmented or single-shot, from GRE (cf. the detailed examples above), Turbo FLASH (also called MPRAGE for brain applications) to Spin Echo (SE) or Turbo Spin Echo (TSE), TrueFisp (also called bSSFP), EPI.

It may also be adapted to any types of MR sequence weighting T1, T2, T2*, ρ (Spin Density), fMRI (functional MRI) or BOLD MRI, and preparation including none-exhaustively, ASL (Arterial Spin Labelling), DWI (Diffusion weighting imaging) with all its variants (DTI, DSI, IVIM, Kurtosis, NODDI), MTR (Magnetization Transfer Ratio) of any type including CEST, quantitative MRI including simultaneous multiparametric technique such as MRF MR Fingerprinting, MR Angiography both static or dynamic. This includes more exotic MRI applications such as MR thermometry or Electromagnetic Property Tomography (EPT).

It has been demonstrated to be compatible with parallel imaging using coil phased array, it is also compatible with Simultaneous Multislice technique.

According to an embodiment of the invention, off-resonance effects due to eddy currents or gradient delays may be corrected. Such imperfections induce discrepancies between the prescribed k-space trajectory (i.e. the output of our algorithm) and the actual one (the one played by the gradient system). Such corrections may for instance be implemented as additional constraints (retrospective correction by updating the definition of the NFFT plan in the data consistency term or SKOPE-based prospective correction: GIRS [Vannejö et al, 2013, Vannejö et al 2016] or blind reconstruction with joint estimation of the impulse response of the gradient waveforms) on the reconstruction iterative algorithm.

In addition, self-navigation extensions (e.g. respiratory) of the proposed approach are rather straightforward to implement [Feng et al, 2016].

An interesting embodiment of the invention is inspired from the "PROPELLER" technique [Pipe et al, 1999]. It consists of sampling the k-space along trajectories having the shape of a candy warp as illustrated on FIG. 15. This allows tracking and correcting the motion of the target body from one spoke to another. Such trajectories enable to sample enough information in the low spatial frequency domain and permit to reconstruct low resolution image from each spoke for further use for in-plane motion correction.

Even more interestingly, the inventive approach is able to take any input target density, not only a variable density but also a uniform in situations where there is no undersampling (e.g. for low matrix size) beyond the Compressed Sensing context.

Until now, only 2D "SPARKLING" trajectories have been considered. However, as mentioned above and as it will be discussed below in more detail, the "SPARKLING" technique can also be adapted to 3D imaging. The inventive sampling approach can be applied straightforwardly to 3D "SPARKLING" trajectories, and more generally to any other kind of 3D non-parametric trajectory.

Figure 17:
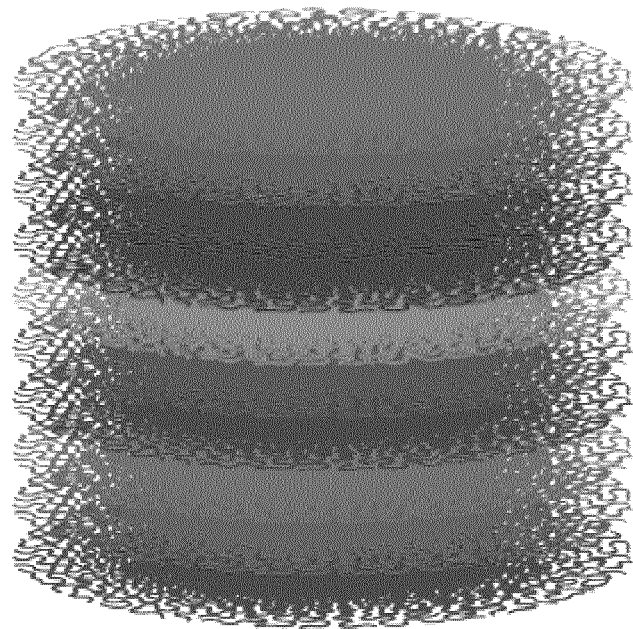

The simplest way of building a 3D "SPARKLING" trajectory is to stack $N_z>1$ identical 2D "SPARKLING" trajectories spaced by a $(FOV_z)^{-1}$ distance ($FOV_z$ being the dimension of the field of view along the stacking direction, $k_z$). FIG. 17 represents a stacking of $N_z=10$ identical 2D "SPARKLING" trajectories filling a cylinder (shades of gray are just for visualization purposes).

More interestingly, to obtain a full 3D variable density, it is possible to stack different 2D "SPARKLING" trajectories, whose target density is changed according to their position along the stacking direction $k_z$. Given a 3D density $\pi \in \mathbb{R}^{N \times N \times N_z}$, a 2D trajectory at position $k_z$ will be generated with density $$\pi_{2D}(k_z) = n(0) \frac{\int \pi(:, :, k_z)}{\int \pi(:, :, 0)}$$

wnere $n(k_z)$ is the number of shot of the plane at position $k_z$. FIG. 18 represents such a variable-density stacking comprising $N_z=11$ different 2D "SPARKLING" trajectories filling a 3D ball. Further acceleration may be reached by subsampling the number of planes and using parallel imaging along the $k_z$ direction.

The "SPARKLING" trajectory generation algorithm of [Boyer et al, 2016] can also be directly generalized to the 3D case, but at the expenses of a very significant increase of the computation time (in a straightforward implementation, the computational complexity of the algorithm is $O(m^2)$, m being the number of samples). The process may be accelerated by truncating the target density into $n_s$ (number of shots) volumetric sectors filling the k-space, and generating one "SPARKLING" trajectory for each sector independently from the others. To further accelerate the process, it is possible to reduce the number of processed shots by taking advantage of a semi-regular partition of a sphere. FIG. 19a shows an equal-area tessellation which divides the surface of a k-space sphere into $n_s=100$ regions ("tiles") of equal areas, each defining a 3D angular sector (e.g. by connecting the center of the sphere with the summits of a tile, see FIG. 19b showing two symmetrical sectors). The property of equal area is important insofar as it ensures that all 3D sectors have equal mass in the case of a radial density. For a constant elevation angle, all tiles—and therefore sectors—are exactly identical and can be obtained from one another using a simple rotation. A "SPARKLING" trajectory may be computed for one sector (FIG. 19c), and the trajectories corresponding to the other sectors of a same elevation angle can be obtained by rotation (FIG. 19d). If symmetric shots for which the echo time is at the middle of the segment are desired, the number of computed trajectories can be further divided by two (this is the case of FIGS. 19b-19d). To avoid discontinuity between the two halves, the sectors are slightly thicked near the origin. In the example of FIGS. 19a-19d, only 7 trajectories have to be computed for generating $n_s=100$ shots.

In an exemplary embodiment, in view of the long computation time required for 3D images, the target density was retrospectively selected among a set of 6 radially decaying densities of the form $$v: k \to \frac{1}{|k|^d},$$

which decays with a decay rate d and is truncated based on a threshold parameter t and give the density $\pi$. Two parameters of the density were varied here: the decay rate de $\{2, 3\}$ and the plateau threshold $\tau \in \{0.5, 0.75, 1\}$. FIG. 20 shows the 6 tested densities for N=320. To rank the different densities, evenlyspaced samples were drawn along each density by using Lloyd's algorithm, also known as Voronoi iteration (Lloyd, 1982), which allows to quickly produce a distribution of points with blue noise characteristics, i.e. to produce a locally uniform coverage. The initial positions of the m samples were determined with an i.i.d. drawing along the considered density. Then, LLoyd's algorithm was applied as follows:

The Voronoi diagram of the m samples was computed.
The centroid of each cell of the Voronoi diagram was computed.
Each sample was then moved to the centroid of its Voronoi cell.

This process was repeated e.g. 10 times. Lloyd's algorithm allowed to spread the samples the clusters that were present in the initial iid sampling were disrupted and void region were filled. In reality, the process is not perfect and some bunches of clusters subsist even after more than 10 iterations.

REFERENCES

[Arias-Castro et al, 2013] E. Arias-Castro, E. J. Candes, and M. Davenport, "On the fundamental limits of adaptive sensing", IEEE Trans. Inf. Theory, 59 (2013), pp. 472-481.

[Beck and Teboulle, 2009] Beck, Amir, and Marc Teboulle. "A fast iterative shrinkage-thresholding algorithm for linear inverse problems." SIAM journal on imaging sciences 2.1 (2009): 183-202.

[Bilgin et al, 2008] Bilgin, A., et al. "Randomly perturbed radial trajectories for compressed sensing MRI." Proc. of ISMRM, Toronto, Canada (2008): 3152.

[Boyer et al, 2016] Boyer, Claire, et al. "On the generation of sampling schemes for magnetic resonance imaging." SIAM Journal on Imaging Sciences 9.4 (2016): 2039-2072.

[Chauffert et al, 2014] Chauffert, Nicolas, et al. "Variable density sampling with continuous trajectories." SIAM Journal on Imaging Sciences 7.4 (2014): 1962-1992.

[Curtis and Anand, 2008] A. T. Curtis and C. K. Anand. Random volumetric MRI trajectories via genetic algorithms, Int. J. Biomed. Imaging, 2008, 6, https://doi.org/10.1155/2008/297089.

[Dippé et Wold, 1985] Dippé, Mark A Z, and Erling Henry Wold. "Antialiasing through stochastic sampling." ACM Siggraph Computer Graphics 19.3 (1985): 69-78.

[Feng et al. 2016] L. Feng, L. Axel, H. Chandarana, K. T. Block, D. K. Sodickson, and R. Otazo, "Xd-grasp: Golden-angle radial MRI with reconstruction of extra motion-state dimensions using compressed sensing," Magnetic resonance in medicine, vol. 75, no. 2, pp. 775-788, 2016.

[Haldar et al, 2011] Haldar, Justin P, Hernando, D. and Liang, Z. P. "Compressed-Sensing MRI with Random Encoding", IEEE Transactiojn of Medical Imaging 30 (2011): 893-903.

[Haldar, 2014] Haldar, Justin P. "Low-Rank Modeling of Local k-Space Neighborhoods (LORAKS) for Constrained MRI", IEEE Transactiojn of Medical Imaging 33.3 (2014): 668-680.

[Lazarus et al, 2017] Lazarus, Carole, et al. "SPARKLING: Novel Non-Cartesian Sampling Schemes for Accelerated 2D Anatomical Imaging at 7T Using Compressed Sensing."

[Liu et al, 2012]: D. D. Liu, D. Liang, X. Liu, and Y.-T. Zhang. Under-sampling trajectory design for compressed sensing MRI, in 2012 Annual International Conference of the IEEE Engineering in Medicine and Biology Society (EMBC), 2012, pp. 73-76.

[Lloyd, 1982]: Stuart Lloyd. "Least squares quantization in PCM". In: IEEE transactions on information theory 28.2 (1982), pp. 129-137 (cit. on p. 87).

[Lustig et al, 2007] Lustig M., Donoho D., Pauly J. M. Sparse MRI: The application of compressed sensing for rapid MR imaging. Magn Reson Med 2007; 58: 1182-1195

[Lustig et al, 2008] Lustig, Michael, et al. "Compressed sensing MRI." IEEE signal processing magazine 25.2 (2008): 72-82.

[Mir et al, 2004] R. Mir, A. Guesalaga, J. Spiniak, M. Guarini, and P. Irarrazaval. Fast three-dimensional k-space trajectory design using missile guidance ideas, Magn. Reson. Med., 52 (2004), pp. 329-336.

[Nayak et al, 1998] Nayak K S, Nishimura D G. Randomized trajectories for reduced aliasing artifact. In: Proceedings of the ISMRM, Sydney, 1998. p 670.

[Pipe et al., 1999] Pipe J G. Motion correction with PROPELLER MRI: application to head motion and free-breathing cardiac imaging. Magn Reson Med 1999; 42:963-9.

[Ravishankar and Bresler, 2011]: S. Ravishankar and Y. Bresler. Adaptive sampling design for compressed sensing MRI, in Annual International Conference of the IEEE Engineering in Medicine and Biology Society, 2011, pp. 3751-3755.

[Seeger et al, 2010] M. Seeger, H. Nickisch, R. Pohmann, and B. Scholkopf. Optimization of k-space trajectories for compressed sensing by Bayesian experimental design. Magn. Reson. Med., 63 (2010), pp. 116-126.

[Spiniak et al, 2005] J. Spiniak, A. Guesalaga, R. Mir, M. Guarini, and P. Irarrazaval. Undersampling k-space using fast progressive 3D trajectories, Magn. Reson. Med., 54 (2005), pp. 886-892.

[Vannesjö et al, 2013] Vannesjö, Signe J., et al. "Gradient system characterization by impulse response measurements with a dynamic field camera." Magnetic resonance in medicine 69.2 (2013): 583-593.

[Vannesjö et al, 2016] Vannesjö, S. Johanna, et al. "Image reconstruction using a gradient impulse response model for trajectory prediction." Magnetic resonance in medicine 76.1 (2016): 45-58.

[Vasanawala et al, 2011] Vasanawala, S. S., et al. "Practical parallel imaging compressed sensing MRI: Summary of two years of experience in accelerating body MRI of pediatric patients." Biomedical Imaging: From Nano to Macro, 2011 IEEE International Symposium on. IEEE, 2011.

[Wang et al, 2004] Wang, Zhou et al. "Image Quality Assessment: From Error Visibility to Structural Similarity" IEEE Transactions on Image Processing, Vol. 13, No. 4, April 2004.

[Wang et al, 2012] Wang, Haifeng, et al. "Smoothed random-like trajectory for compressed sensing MRI." Engineering in Medicine and Biology Society (EMBC), 2012 Annual International Conference of the IEEE. IEEE, 2012.

The invention claimed is:

1. A method of performing magnetic resonance imaging of a body comprising the steps of:
   a) immerging the body (BD) in a static and substantially uniform magnetic field (BO), called longitudinal field oriented along a direction (z), called longitudinal direction;
   b) transmitting to said body a plurality of radio-frequency pulse (RFP) adapted for exciting nuclear spins inside said body;
   c) after each said radio-frequency pulse, applying to said body a time-varying magnetic field gradient ($G_x$, $G_y$) defining a respective non-parametric trajectory (ST) in a k-space and simultaneously acquiring samples of a magnetic resonance signal emitted by the excited nuclear spin, each sample corresponding to a point ($K_i$, KS) of the k-space belonging to said trajectory, wherein the points of the k-space corresponding to the samples define a pseudo-random sampling of the k-space, following a predetermined sampling density; and
   d) applying a sparsity-promoting nonlinear reconstruction algorithm to the acquired samples for reconstructing a magnetic resonance image of said body, said image being formed by a two-dimensional, three-dimensional or four-dimensional array of pixels;
      the number of non-parametric trajectories in the k-space, each following a respective radio-frequency pulse, along which said samples are acquired, being lower than the number of pixels or voxels along one direction of said array;
      wherein
         a number of samples along each of said trajectories exceeds a number of pixels along at least one dimension of said array; and in that:
      at least in a central region of the k-space, the distance ($\Delta k$) between any two adjacent points belonging to a same trajectory is lower than 1/FOV, FOV being a size of a field of view of the reconstructed image of the object.

2. The method of claim 1, wherein step c further comprises determining the points of the k-space belonging to said or each trajectory by projecting a predetermined sampling density distribution onto a set of discrete pushforward measures.

3. The method of claim 2, wherein said set of discrete pushforward measures is constituted by the pushforward measures defined on all continuous trajectories in the k-space corresponding to time-varying magnetic field gradients whose maximum amplitude and maximum slew rate do not exceed respective limits.

4. The method of claim 1, wherein said step d) comprises reconstructing a magnetic resonance image of said body by optimizing a nonlinear sparsity-promoting criterion, function of the acquired samples, said optimizing being performed using a Fast Iterative Soft Thresholding Algorithm.

5. The method of claim 1, performed using a magnetic resonance imaging apparatus, wherein, during step c), said applying to said body a time-varying magnetic field gradient ($G_x$, $G_y$) defining a non-parametric trajectory (ST) in a k-space is carried out using a minimum gradient raster time for said magnetic resonance imaging apparatus.

6. A magnetic resonance imaging apparatus comprising:
- a first coil (LC) suitable for generating a static magnetic field (B0), called longitudinal field, substantially uniform within a volume of interest and oriented along a direction, called longitudinal direction;
- a set of gradient coils (CGx, CGy, CGz) suitable for generating, within said volume of interest, a time-varying magnetic field gradient;
- at least one radio-frequency coils (TC) suitable for generating a radio-frequency pulse within said volume of interest; and
- a control unit (CU) configured or programmed to drive said gradient coils and said radio-frequency coil or coils, and to acquire and process signals received by said radio-frequency coil or coils, to carry out a method according to claim 1.

* * * * *

UNITED STATES PATENT AND TRADEMARK OFFICE
CERTIFICATE OF CORRECTION

| | |
|---|---|
| PATENT NO. | : 11,937,908 B2 |
| APPLICATION NO. | : 16/639725 |
| DATED | : March 26, 2024 |
| INVENTOR(S) | : Nicolas Chauffert et al. |

It is certified that error appears in the above-identified patent and that said Letters Patent is hereby corrected as shown below:

On the Title Page

In (73):
"COMMISSARIAT A L'ENERGIE ATOMIQUE ET AUX ENERGIES ALTERNATIVES PARIS, FRANCE, Paris (FR);"
Should be:
--COMMISSARIAT A L'ENERGIE ATOMIQUE ET AUX ENERGIES ALTERNATIVES, Paris (FR);--.

Signed and Sealed this
Fourteenth Day of May, 2024

Katherine Kelly Vidal
*Director of the United States Patent and Trademark Office*